(12) United States Patent
Riley et al.

(10) Patent No.: US 6,518,017 B1
(45) Date of Patent: Feb. 11, 2003

(54) COMBINATORIAL ANTISENSE LIBRARY

(75) Inventors: Timothy A. Riley, San Diego, CA (US); Bob D. Brown, San Diego, CA (US); Lyle J. Arnold, San Diego, CA (US)

(73) Assignee: Oasis Biosciences Incorporated, San Diego, CA (US)

( * ) Notice: Subject to any disclaimer, the term of this patent is extended or adjusted under 35 U.S.C. 154(b) by 0 days.

(21) Appl. No.: 09/136,080

(22) Filed: Aug. 18, 1998

Related U.S. Application Data

(60) Provisional application No. 60/060,673, filed on Oct. 2, 1997.

(51) Int. Cl.$^7$ .......................... C12Q 1/68; C07H 21/00; C07H 21/04
(52) U.S. Cl. .......................... 435/6; 435/325; 435/375; 435/455; 536/23.1; 536/24.5
(58) Field of Search .................. 435/6, 91.1, 91.31, 435/455, 183, 199, 325, 375, 252.3, 320.1; 536/23.1, 24.3, 24.33, 24.5, 25.3, 25.32

(56) References Cited

U.S. PATENT DOCUMENTS

| | | | |
|---|---|---|---|
| 5,112,974 A | * | 5/1992 | Barton ........................... 546/4 |
| 5,424,413 A | | 6/1995 | Hogan et al. |
| 5,438,131 A | | 8/1995 | Bergstrom et al. |
| 5,571,902 A | * | 11/1996 | Ravikumar et al. |
| 5,612,215 A | * | 3/1997 | Draper et al. |
| 5,677,289 A | | 10/1997 | Torrence et al. |
| 5,681,947 A | * | 10/1997 | Bergstrom et al. ......... 536/28.6 |
| 5,686,242 A | | 11/1997 | Bruice et al. |
| 5,700,922 A | | 12/1997 | Cook |
| 5,719,271 A | * | 2/1998 | Cook et al. ................. 536/23.1 |
| 5,728,818 A | | 3/1998 | Wincott et al. |
| 5,843,650 A | | 12/1998 | Segev |
| 6,150,141 A | * | 11/2000 | Jarrell |

FOREIGN PATENT DOCUMENTS

| | | |
|---|---|---|
| WO | WO96/32474 | 10/1996 |
| WO | WO97/38097 | 10/1997 |

OTHER PUBLICATIONS

Pierce, M.L. et al. Nucleic Acids Research, 1998, vol. 26, No. 22, pp. 5093–5101.*

Milligan, J.F. et al. Journal of Medicinal Chemistry, Jul. 9, 1993, vol. 36, No. 14, pp. 1923–1937.*

Hendry, R. et al., "Using Linkers to investigate the spatial separation of the conserved nucleotides A9 and G12 in the hammerhead ribozyme", *Biochimica et Biophysical Acta* (Oct. 18, 1994) 1219(2):405–412.

Krupp, G., "Antisense oligoribonucleotides and RNase P. A Great Potential", *Biochimi* (1993) 75(½):135–139.

Lieber, A. et al., "Selection of Efficient Cleavage Sites in Target RNAs by Using a Ribozyme Expression Library", *Molecule and Cellular Biology* (Jan. 1995) 15(1):540–551.

Reynolds, M.A. et al., "Antisense Oligonucleotides Containing an Internal, Non–nucleotide–based Linker Promote Site–Specific Cleavage of RNA", *Nucleic Acids Research* (Feb. 15, 1996) 24(4):760–765.

Benseler et al., "Hammerhead–like Molecules Containing Non–Nucleotide Linkers Are Active RNA Catalysts", (1993) *J. Am. Chem. Soc.* 115:8483–8484.

* cited by examiner

*Primary Examiner*—John L. LeGuyader
*Assistant Examiner*—Mary M Schmidt
(74) *Attorney, Agent, or Firm*—Knobbe, Martens, Olson & Bear, LLP

(57) ABSTRACT

Combinatorial libraries comprise first oligonucleotide analogs and second oligonucleotide analogs which are coupled together to form antisense molecules capable of binding target polynucleotides and activating an RNase, and ribozymes capable of cleaving polynucleotides.

7 Claims, 2 Drawing Sheets

SEQUENCE LISTING

<160> NUMBER OF SEQ ID NOS: 54

<210> SEQ ID NO 1
<211> LENGTH: 14
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (3)...(7)
<223> OTHER INFORMATION: n=a, g, c or u

<400> SEQUENCE: 1
ggnnnnncug auga                                                              14

<210> SEQ ID NO 2
<211> LENGTH: 8
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (4)...(8)
<223> OTHER INFORMATION: n=a, g, c or t

<400> SEQUENCE: 2 gaannnnn                                                                      8

<210> SEQ ID NO 3
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 3
cgaaattaaa tcgactcact at                                                     22

<210> SEQ ID NO 4
<211> LENGTH: 80
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA

<400> SEQUENCE: 4
caggcccagc agcagcagca gcagcagcat ggtgggcgaa ttcgcgattc gaagccctat            60
agtgagtcgt attaatttcg                                                        80

<210> SEQ ID NO 5
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 5
ggttctcctc ctcaactggg at                                                     22

<210> SEQ ID NO 6
<211> LENGTH: 76
<212> TYPE: DNA
<213> ORGANISM: Artificial Sequence
<220> FEATURE:

<223> OTHER INFORMATION: synthetic oligonucleotide

<400> SEQUENCE: 6
ggttctcctc ctcaactggg atgatgccca gggagagctg tagcctcagg cccagcagca    60
gcagcagcag cagcat                                                    76

<210> SEQ ID NO 7
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 7
gggcttcgaa tcgcgaattc gcccaccatg ctgctgctgc tgctgctgct gggcctgagg    60
ctacagctct ccctgggcat catcccagtt gaggaggaga acc                     103

<210> SEQ ID NO 8
<211> LENGTH: 30
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (15)...(15); (16)...(16)
<223> OTHER INFORMATION: Glen Research spacer 9 (cat #11-1909-90)
      between c 15 and g 16

<400> SEQUENCE: 8
gcugguugag uacucggugg gcgaauucgc                                     30

<210> SEQ ID NO 9
<211> LENGTH: 27
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (15)...(15); (16)...(16)
<223> OTHER INFORMATION: Glen research spacer 9 (cat # 10-1909-90)
      between c 15 and g 16

<400> SEQUENCE: 9
gcugguugag uacucggugg gcgaauu                                        27

<210> SEQ ID NO 10
<211> LENGTH: 23
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (15)...(15); (16)...(16)
<223> OTHER INFORMATION: Glen research spacer 9 (cat # 10-1909-90)
      between c 15 and g 16

<400> SEQUENCE: 10
gcugguugag uacucggugg gcg                                            23

<210> SEQ ID NO 11
<211> LENGTH: 21
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (15)...(15); (16)...(16)

-continued

```
<223> OTHER INFORMATION: Glen research spacer 9 (cat # 10-1909-90)
      between c 15 and g 16

<400> SEQUENCE: 11
gcugguugag uacucggugg g                                              21

<210> SEQ ID NO 12
<211> LENGTH: 19
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (15)...(15); (16)...(16)
<223> OTHER INFORMATION: Glen research spacer 9 (cat # 10-1909-90)
      between c 15 and g 16

<400> SEQUENCE: 12
gcugguugag uacucggug                                                 19

<210> SEQ ID NO 13
<211> LENGTH: 25
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (1)...(1)
<223> OTHER INFORMATION: Rhodamine-labeled guanine

<400> SEQUENCE: 13
gcagcagcat gaguacucaa ccagc                                          25

<210> SEQ ID NO 14
<211> LENGTH: 25
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (1)...(1)
<223> OTHER INFORMATION: Fluorescein-labeled guanine

<400> SEQUENCE: 14
gcugguugag uacucggugg gcgaa                                          25

<210> SEQ ID NO 15
<211> LENGTH: 27
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (12)...(12); 13)...(13)
<223> OTHER INFORMATION: Glen research spacer 9 (cat # 10-1909-90)
      between t 12 and g 13

<400> SEQUENCE: 15
cagcagcagc atgaguacuc aaccagc                                        27

<210> SEQ ID NO 16
<211> LENGTH: 25
<212> TYPE: DNA
<213> ORGANISM: Artificial Sequence
<220> FEATURE:
<223> OTHER INFORMATION: synthetic oligonucleotide
```

```
<223> OTHER INFORMATION: combined DNA/RNA
<221> NAME/KEY: misc_feature
<222> LOCATION: (10)...(10); (11)...(11)
<223> OTHER INFORMATION: Glen research spacer 9 (cat # 10-1909-90)
      between t 10 and g 11

<400> SEQUENCE: 16
gcagcagcat gaguacucaa ccagc                                          25

<210> SEQ ID NO 17
<211> LENGTH: 23
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (8)...(8); (9)...(9)
<223> OTHER INFORMATION: Glen research spacer 9 (cat # 10-1909-90)
      between t 8 and g 9

<400> SEQUENCE: 17
agcagcatga guacucaacc agc                                            23

<210> SEQ ID NO 18
<211> LENGTH: 21
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (6)...(6); (7)...(7)
<223> OTHER INFORMATION: Glen research spacer 9 (cat # 10-1909-90)
      between t 6 and g 7

<400> SEQUENCE: 18
cagcatgagu acucaaccag c                                              21

<210> SEQ ID NO 19
<211> LENGTH: 19
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (4)...(4); (5)...(5)
<223> OTHER INFORMATION: Glen research spacer 9 (cat # 10-1909-90)
      between t 4 and g 5

<400> SEQUENCE: 19
gcatgaguac ucaaccagc                                                 19

<210> SEQ ID NO 20
<211> LENGTH: 21
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature

<400> SEQUENCE: 20
cagcatgagu acucaaccag c                                              21

<210> SEQ ID NO 21
<211> LENGTH: 30
<212> TYPE: RNA
```

```
<213> ORGANISM: Artificial Sequence
<220> FEATURE:
<223> OTHER INFORMATION: synthetic oligonucleotide
<221> NAME/KEY: misc_feature
<222> LOCATION: (15)...(15); (16)...(16)
<223> OTHER INFORMATION: Glen research spacer 9 (cat # 10-1909-90)
      between c 15 and g 16

<400> SEQUENCE: 21
gcugguugag uacucggugg gcgaauucgc                              30

<210> SEQ ID NO 22
<211> LENGTH: 27
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (15)...(15); (16)...(16)
<223> OTHER INFORMATION: Glen research spacer 9 (cat # 10-1909-90)
      between c 15 and g 16

<400> SEQUENCE: 22
gcugguugag uacucggugg gcgaauu                                 27

<210> SEQ ID NO 23
<211> LENGTH: 25
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (15)...(15); (16)...(16)
<223> OTHER INFORMATION: Glen research spacer 9 (cat # 10-1909-90)
      between c 15 and g 16

<400> SEQUENCE: 23
gcugguugag uacucggugg gcgaa                                   25

<210> SEQ ID NO 24
<211> LENGTH: 23
<212> TYPE: RNA
<213> ORGANISM: Artificial Sequence
<220> FEATURE:
<223> OTHER INFORMATION: synthetic oligonucleotide
<221> NAME/KEY: misc_binding
<222> LOCATION: (15)...(15); (16)...(16)
<223> OTHER INFORMATION: Glen research spacer 9 (cat # 10-1909-90)
      between c 15 and g 16

<400> SEQUENCE: 24
gcugguugag uacucggugg gcg                                     23

<210> SEQ ID NO 25
<211> LENGTH: 21
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (15)...(15); (16)...(16)
<223> OTHER INFORMATION: Glen research spacer 9 (cat # 10-1909-90)
      between c 15 and g 16

<400> SEQUENCE: 25
gcugguugag uacucggugg g                                       21

<210> SEQ ID NO 26
<211> LENGTH: 19
```

```
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (15)...(15); (16)...(16)
<223> OTHER INFORMATION: Glen research spacer 9 (cat # 10-1909-90)
      between c 15 and g 16

<400> SEQUENCE: 26
gcugguugag uacucggug                                              19

<210> SEQ ID NO 27
<211> LENGTH: 23
<212> TYPE: RNA
<213> ORGANISM: Artificial Sequence
<220> FEATURE:
<223> OTHER INFORMATION: synthetic oligonucleotide

<400> SEQUENCE: 27
gcugguugag uacucggugg gcg                                         23

<210> SEQ ID NO 28
<211> LENGTH: 30
<212> TYPE: RNA
<213> ORGANISM: Artificial Sequence
<220> FEATURE:
<223> OTHER INFORMATION: synthetic oligonucleotide
<221> NAME/KEY: misc_binding
<222> LOCATION: (15)...(15); (16)...(16)
<223> OTHER INFORMATION: Glen research spacer 9 (cat # 10-1909-90)
      between c 15 and g 16
<222> LOCATION: (30)...(30)
<223> OTHER INFORMATION: n=propyl linker attached to c 30

<400> SEQUENCE: 28
gcugguugag uacucggugg gcgaauucgc                                  30

<210> SEQ ID NO 29
<211> LENGTH: 23
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (5)...(8)
<223> OTHER INFORMATION: n=universal base
<222> LOCATION: (8)...(8); (9)...(9)
<223> OTHER INFORMATION: Glen research spacer 9 (cat # 10-1909-90)
      between n 8 and g 9

<400> SEQUENCE: 29 agcannnga guacucaacc agc                                          23

<210> SEQ ID NO 30
<211> LENGTH: 23
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (7)...(8)
<223> OTHER INFORMATION: n=universal base
<222> LOCATION: (8)...(8); (9)...(9)
<223> OTHER INFORMATION: Glen research spacer 9 (cat # 10-1909-90)
      between n 8 and g 9

<400> SEQUENCE: 30
agcagcnnga guacucaacc agc                                         23
```

```
<210> SEQ ID NO 31
<211> LENGTH: 23
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (1)...(4)
<223> OTHER INFORMATION: n=universal base
<222> LOCATION: (8)...(8); (9)...(9)
<223> OTHER INFORMATION: Glen research spacer 9 (cat # 10-1909-90)
      between t 8 and g 9

<400> SEQUENCE: 31
nnnngcatga guacucaacc agc                                              23

<210> SEQ ID NO 32
<211> LENGTH: 23
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (1)...(2)
<223> OTHER INFORMATION: n=purine mimic
<222> LOCATION: (3)...(3)
<223> OTHER INFORMATION: n=pyrimidine mimic
<222> LOCATION: (4)...(5)
<223> OTHER INFORMATION: n=purine mimic
<222> LOCATION: (6)...(6)
<223> OTHER INFORMATION: n=pyrimidine mimic
<222> LOCATION: (7)...(7)
<223> OTHER INFORMATION: n=purine mimic
<222> LOCATION: (8)...(8)
<223> OTHER INFORMATION: n=pyrimidine mimic
<222> LOCATION: (9)...(9)
<223> OTHER INFORMATION: Glen research spacer 9 (cat # 10-1909-90)
      between n 8 and g 9

<400> SEQUENCE: 32
nnnnnnnnga guacucaacc agc                                              23

<210> SEQ ID NO 33
<211> LENGTH: 23
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (1)...(2)
<223> OTHER INFORMATION: n=purine mimic
<222> LOCATION: (3)...(3)
<223> OTHER INFORMATION: n=pyrimidine mimic
<222> LOCATION: (4)...(4)
<223> OTHER INFORMATION: n=purine mimic
<222> LOCATION: (9)...(9)
<223> OTHER INFORMATION: Glen research spacer 9 (cat # 10-1909-90)
      between t 8 and g 9

<400> SEQUENCE: 33
nnnngcatga guacucaacc agc                                              23

<210> SEQ ID NO 34
<211> LENGTH: 14
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
```

```
<222> LOCATION: (6)...(6); (7)...(7)
<223> OTHER INFORMATION: Glen research spacer 9 (cat # 10-1909-90)
     between t 6 and g 7
<222> LOCATION: (14)...(14)
<223> OTHER INFORMATION: propyl linker attached to g 14

<400> SEQUENCE: 34
cagcatggug ggcg                                                      14

<210> SEQ ID NO 35
<211> LENGTH: 16
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (4)...(5); (5)...(5)
<223> OTHER INFORMATION: Glen research spacer 9 (cat # 10-1909-90)
     between t 4 and g 5
<222> LOCATION: (16)...(16)
<223> OTHER INFORMATION: propyl linker

<400> SEQUENCE: 35
gcatgguggg cgaauu                                                    16

<210> SEQ ID NO 36
<211> LENGTH: 20
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (5)...(8)
<223> OTHER INFORMATION: n=universal base
<222> LOCATION: (8)...(8); 9)...(9)
<223> OTHER INFORMATION: Glen research spacer 9 (cat # 10-1909-90)
     between n 8 and g 9
<222> LOCATION: (20)...(20)
<223> OTHER INFORMATION: propyl linker attached to u 20

<400> SEQUENCE: 36
agcannnngg ugggcgaauu                                                20

<210> SEQ ID NO 37
<211> LENGTH: 16
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (3)...(4)
<223> OTHER INFORMATION: n=universal base
<222> LOCATION: (4)...(4); (5)...(5)
<223> OTHER INFORMATION: Glen research spacer 9 (cat # 10-1909-90)
     between n 4 and g 5
<222> LOCATION: (16)...(16)
<223> OTHER INFORMATION: propyl linker attached to u 16

<400> SEQUENCE: 37 gcnnguggg cgaauu                                                     16

<210> SEQ ID NO 38
<211> LENGTH: 27
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (13)...(13)
```

```
<223> OTHER INFORMATION: Glen research spacer 9 (cat # 10-1909-90)
      between t 12 and g 13
<222> LOCATION: (27)...(27)
<223> OTHER INFORMATION: propyl linker attached to c 27

<400> SEQUENCE: 38
gttctcgctg gtgaguacuc aaccagc                                              27

<210> SEQ ID NO 39
<211> LENGTH: 23
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (15)...(15); (16)...(16)
<223> OTHER INFORMATION: Glen research spacer 9 (cat # 10-1909-90)
      between c 15 and g 16

<400> SEQUENCE: 39
gcugguugag uacucgaguu uca                                                  23

<210> SEQ ID NO 40
<211> LENGTH: 27
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (12)...(12); (13)...(13)
<223> OTHER INFORMATION: Glen research spacer 9 (cat # 10-1909-90)
      between c 12 and g 13
<222> LOCATION: (27)...(27)
<223> OTHER INFORMATION: propyl linker attached to c 27

<400> SEQUENCE: 40
tgtgttacca tcgaguacuc aaccagc                                              27

<210> SEQ ID NO 41
<211> LENGTH: 23
<212> TYPE: RNA
<213> ORGANISM: Artificial Sequence
<220> FEATURE:
<223> OTHER INFORMATION: synthetic oligonucleotide
<221> NAME/KEY: misc_feature
<222> LOCATION: (15)...(15); (16)...(16)
<223> OTHER INFORMATION: Glen research spacer 9 (cat # 10-1909-90)
      between c 15 and g 16

<400> SEQUENCE: 41
gcugguugag uacucgguug cgu                                                  23

<210> SEQ ID NO 42
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 42
gttctcgctg gtgagtttca                                                      20

<210> SEQ ID NO 43
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 43
ggttttacca tcggttctgg                                              20

<210> SEQ ID NO 44
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 44
tctacccgcg tccggcat                                                18

<210> SEQ ID NO 45
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 45
tctcccagcg tgcgccat                                                18

<210> SEQ ID NO 46
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 46
tctacccgcg tccggcat                                                18

<210> SEQ ID NO 47
<211> LENGTH: 27
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (12)...(12); (13)...(13)
<223> OTHER INFORMATION: Glen research spacer 9 (cat # 10-1909-90)
      between g 12 and g 13
<222> LOCATION: (27)...(27)
<223> OTHER INFORMATION: propyl linker attached to c 27

<400> SEQUENCE: 47
tctcccagcg tggaguacuc aaccagc                                      27

<210> SEQ ID NO 48
<211> LENGTH: 27
<212> TYPE: DNA
<213> ORGANISM: Artificial Sequence
<220> FEATURE:
<223> OTHER INFORMATION: synthetic oligonucleotide
<223> OTHER INFORMATION: combined DNA/RNA
<221> NAME/KEY: misc_feature
<222> LOCATION: (11)...(12)
<223> OTHER INFORMATION: n=universal base
<222> LOCATION: (12)...(12); (13)...(13)
<223> OTHER INFORMATION: Glen research spacer 9 (cat # 10-1909-90)
      between n 12 and n 13
<222> LOCATION: (27)...(27)
<223> OTHER INFORMATION: propyl linker attached at c 27

<400> SEQUENCE: 48

```
tctcccagcg nngaguacuc aaccagc                                    27
```

<210> SEQ ID NO 49
<211> LENGTH: 21
<212> TYPE: DNA
<213> ORGANISM: Artificial Sequence
<220> FEATURE:
<223> OTHER INFORMATION: synthetic oligonucleotide
<221> NAME/KEY: misc_feature
<222> LOCATION: (16)...(16)
<223> OTHER INFORMATION: Glen research spacer 9 (cat # 10-1909-90)
      between c 15 and c 16
<222> LOCATION: (21)...(21)
<223> OTHER INFORMATION: propyl linker attached to t 21

<400> SEQUENCE: 49

```
gcugguugag uacuccgcca t                                          21
```

<210> SEQ ID NO 50
<211> LENGTH: 53
<212> TYPE: RNA
<213> ORGANISM: Artificial Sequence
<220> FEATURE:
<223> OTHER INFORMATION: synthetic oligonucleotide

<400> SEQUENCE: 50

```
gggcuucgaa ucgcgaauuc gcccaccaug cugcugcugc ugcugcugcu gcu       53
```

<210> SEQ ID NO 51
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 51

```
ggtgccacct gtggtccacc tg                                         22
```

<210> SEQ ID NO 52
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 52

```
cttcacttgt ggcccagata gg                                         22
```

<210> SEQ ID NO 53
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 53

```
gagctgcgtg tggctcccga gg                                         22
```

<210> SEQ ID NO 54
<211> LENGTH: 27
<212> TYPE: DNA
<213> ORGANISM: Artificial Sequence -continued

```
<220> FEATURE:
<223> OTHER INFORMATION: synthetic oligonucleotide

<400> SEQUENCE: 54
cgcaggatgg catgggggc atacccc                                        27
```

COMBINATORIAL ANTISENSE LIBRARY

RELATED APPLICATIONS

This application claims priority from US Provisional Application Serial No. 60/060,673, filed Oct. 2, 1997.

FIELD OF THE INVENTION

This invention relates generally to the fields of organic chemistry and biological assays. More specifically, the invention relates to methods and compositions for determining optimal antisense sequences, and optimized libraries of oligonucleotide analogs.

BACKGROUND OF THE INVENTION

Antisense technology is based on the finding that DNA and/or RNA transcription or translation can be modulated using an oligonucleotide which binds to the target nucleic acid. By exploiting the Watson-Crick base pairing, one can design antisense molecules having a very high degree of specificity for the target nucleic acid. Oligonucleotides having only standard ("natural") bases and backbones must in general contain at least 17 bases in order to bind with sufficient energy to effectively down-regulate gene expression by activating RNase H.

However, even given DNA or RNA of known sequence, it is still difficult to design an optimally effective antisense molecule. This is because nucleic acids are subject to the formation of a variety of secondary and tertiary structures in vivo, and are frequently coiled, supercoiled, folded, and/or obscured by proteins. Some portions of the target sequence are much more susceptible to binding and hybridization by antisense molecules, while other portions of the target sequence are essentially hidden or unavailable. Typically, 20 to 50 oligonucleotides are tested to find one or more active antisense sites per gene.

Standard methods for selecting antisense sites within pre-mRNA or mRNA sequences are insufficient for the rapid, high-throughput application of antisense to large scale target validation programs. Oligonucleotides must be "custom-synthesized" for each target site within each target gene. A standing library of millions or billions of conventional oligonucleotides would be required to successfully target each of the approximately 100,000 human genes. An ordered library of millions of antisense oligonucleotides is beyond the chemical, physical, and organizational tools currently available.

SUMMARY OF THE INVENTION

A new method for preparing and testing antisense and ribozyme sequences has now been invented.

One aspect of the invention is a composition comprising two oligonucleotide analogs, each having a binding domain and a coupling moiety, wherein the binding domains are capable of hybridizing to a target polynucleotide, and the coupling moieties are capable of coupling to each other in the absence of a target molecule.

Another aspect of the invention is a compound of the formula $R_1$—$L_1$—X—A—Y—$L_2$—$R_2$, wherein $R_1$ is an oligonucleotide, or an oligonucleotide analog, capable of binding to $_{RNA;}$ $R_2$ is an oligonucleotide, or an oligonucleotide analog, capable of binding to RNA; $L_1$ and $L_2$ are each independently a linking moiety or a bond; X and Y are each independently a coupling moiety; and A comprises a link selected from the group consisting of a covalent bond, a metal ion, and a non-covalent bond, wherein said compound is capable of activating a nuclease or catalyzing cleavage when bound to a target polynucleotide.

Another aspect of the invention is a method for cleaving a target polynucleotide, comprising providing a target RNA molecule; contacting the target RNA molecule with a first oligonucleotide analog, comprising a first binding domain capable of binding a first region of a target polynucleotide, and a first coupling moiety capable of binding to a second coupling moiety, and a second oligonucleotide analog, comprising a second binding domain capable of binding a second region of said target polynucleotide, and a second coupling moiety capable of binding to said first coupling moiety, wherein said first and second binding domains are capable of binding simultaneously to said target RNA molecule; and incubating said target RNA molecule, first analog and second analog in the presence of an RNase capable of cleaving the RNA target.

Another aspect of the invention is a method for cleaving a target RNA molecule, comprising providing a target RNA molecule; contacting the target RNA molecule with a first oligonucleotide analog, comprising a first binding domain capable of binding a first region of a target polynucleotide, and a first coupling moiety capable of binding to a second coupling moiety, and a second oligonucleotide analog, comprising a second binding domain capable of binding a second region of said target polynucleotide, and a second coupling moiety capable of binding to said first coupling moiety, wherein said first and second binding domains are capable of binding simultaneously to said target RNA molecule; and incubating said target RNA molecule, first analog and second analog in the presence of an RNase capable of cleaving the RNA target.

Another aspect of the invention is an antisense library, comprising a set of first oligonucleotide analogs, each first analog comprising a first coupling moiety and a first binding domain, said first binding domain comprising a first backbone and a plurality of first bases capable of base-pairing with a target nucleic acid; and a set of second oligonucleotide analogs, each second analog comprising a second coupling moiety capable of coupling specifically to said first coupling moiety, and a second binding domain, said second binding domain comprising a second backbone and a plurality of second bases capable of base-pairing with a target nucleic acid; wherein an antisense analog consisting of a first analog coupled to a second analog is capable of binding to a target nucleic acid and serving as a nuclease substrate.

Another aspect of the invention is a library of antisense precursor compounds, a plurality of compounds of formula 2 ($R_1$—$L_1$—X) and a plurality of compounds of formula 3 (Y—$L_2$—$R_2$), wherein $R_1$ and $R_2$ are each independently an oligonucleotide or an oligonucleotide analog, capable of binding to mRNA; $L_1$ and $L_2$ are each independently a linking moiety or a bond; X and Y are each independently a coupling moiety; and wherein said compounds of formula 2 and formula 3 can be coupled to form a compound capable of recruiting or activating a nuclease when bound to a target polynucleotide.

Another aspect of the invention is a library of ribozyme precursor compounds, comprising a plurality of compounds of formula 4 (GG-$R_1$-CUGAUGA-$L_1$-X) and a plurality of compounds of formula 5 (Y-$L_2$-GAA-$R_2$), wherein $R_1$ and $R_2$ are each independently an oligonucleotide or an oligonucleotide analog, capable of binding to RNA; $L_1$ and $L_2$ are each independently a linking moiety or a bond; X and Y are each independently a coupling moiety; and wherein said compounds of formula 4 and formula 5 can be coupled to form a ribozyme.

Another aspect of the invention is a method for determining an optimal antisense site for a given mRNA, comprising: selecting a plurality of first oligonucleotide analogs, said first analogs comprising a first coupling moiety and a first binding domain which is complementary to said mRNA; selecting a second oligonucleotide analog for each first oligonucleotide analog, said second analog comprising a second coupling moiety capable of binding said first coupling moiety, and a second binding domain which is complementary to said RNA at a position proximal to the site to which said first binding domain is complementary; coupling said first coupling moieties and said second moieties to provide a plurality of antisense probes; contacting said mRNA with said antisense probes in the presence of an RNase to form a cleavage product; and determining which antisense probe corresponds to said cleavage product.

Another aspect of the invention is a method for determining an optimal ribozyme cleavage site for a given target RNA, comprising: selecting a plurality of first oligonucleotide analogs, said first analogs comprising a first coupling moiety and a first binding domain which is complementary to said target RNA; selecting a second oligonucleotide analog for each first oligonucleotide analog, said second analog comprising a second coupling moiety capable of binding said first coupling moiety, and a second binding domain which is complementary to said RNA at a position proximal to the site to which said first binding domain is complementary; coupling said first coupling moieties and said second moieties to provide a plurality of ribozymes; contacting said target RNA with said ribozymes to form a cleavage product; and determining which ribozyme corresponds to said cleavage product.

One object of the invention is to provide a method for preparing antisense or ribozyme molecules quickly, using a feasible number of pre-synthesized components.

Another object of the invention is to provide a library of components suitable for forming antisense or ribozyme molecules on demand.

Another object of the invention is to provide methods for determining the optimal antisense or ribozyme sequence for a given target.

Another object of the invention is to provide methods for determining an antisense or ribozyme sequence when the target polynucleotide sequence is unknown.

DETAILED DESCRIPTION

Definitions

Figure 1:
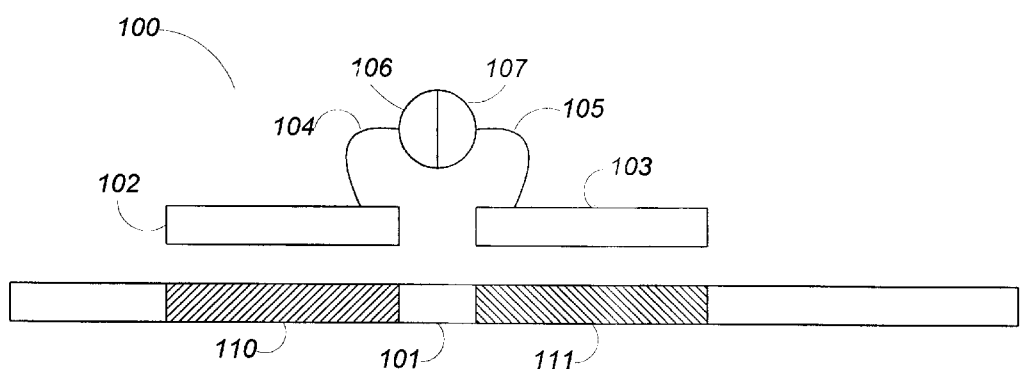
FIG. 1 schematically depicts an oligonucleotide construct of the invention.

The term "antisense" as used herein refers to a molecule designed to interfere with gene expression and capable of recognizing or binding to a specific desired target polynucleotide sequence. Antisense molecules typically (but not necessarily) comprise an oligonucleotide or oligonucleotide analog capable of binding specifically to a target sequence present on an RNA molecule. Such binding interferes with translation by a variety of means, including preventing the action of polymerases, RNA processing and recruiting and/or activating nucleases.

The term "ribozyme" as used herein refers to an oligonucleotide or oligonucleotide analog capable of catalytically cleaving a polynucleotide.

The term "oligonucleotide" refers to a molecule consisting of DNA, RNA, or DNA/RNA hybrids.

The term "oligonucleotide analog" refers to a molecule comprising an oligonucleotide-like structure, for example having a backbone and a series of bases, wherein the backbone and/or one or more of the bases can be other than the structures found in naturally-occurring DNA and RNA. "Non-natural" oligonucleotide analogs include at least one base or backbone structure that is not found in natural DNA or RNA. Exemplary oligonucleotide analogs include, without limitation, DNA, RNA, phosphorothioate oligonucleotides, peptide nucleic acids ("PNA"s), methoxyethyl phosphorothioates, oligonucleotides containing deoxyinosine or deoxy 5-nitroindole, and the like.

The term "oligomer" as used herein refers to a component of the invention comprising a binding domain and at least one coupling moiety. The oligomer can be bound to the coupling moiety optionally with a flexible linker. Oligomers can be represented generically by the formula Y—$L_1$—R—$L_2$—X, where R is a binding domain, $L_1$ and $L_2$ are each independently an optional flexible linker, X is a coupling moiety, and Y is an optional second coupling moiety. Oligomers can further comprise detectable labels. Individual oligomers can be too short to exhibit activity, but are capable of exhibiting activity when coupled.

The term "library" refers to a collection of components that can be joined to form a variety of different antisense molecules. In the practice of the invention, a library comprises at least two sets of oligomers, designed such that oligomers of the first set can couple to oligomers of the second set, preferably spontaneously on addition.

The term "backbone" as used herein refers to a generally linear molecule capable of supporting a plurality of bases attached at defined intervals. Preferably, the backbone will support the bases in a geometry conducive to hybridization between the supported bases and the bases of a target polynucleotide.

The term "unnatural base" refers to a base other than A, C, G, T, and U, and includes degenerate and universal bases as well as moieties capable of binding specifically to a natural base or another unnatural base.

The term "universal base" refers to a moiety that may be substituted for any base. The universal base need not contribute to hybridization, but should not significantly detract from hybridization. Exemplary universal bases include, without limitation, inosine, 5-nitroindole and 4-nitrobenzimidazole.

The term "degenerate base" refers to a moiety that is capable of base-pairing with either any purine, or any pyrimidine, but not both purines and pyrimidines. Exemplary degenerate bases include, without limitation, 6H,8H-3,4-dihydropyrimido[4,5-c][1,2]-oxazin-7-one ("P", a pyrimidine mimic) and 2-amino-6-methoxyaminopurine ("K", a purine mimic).

The term "target polynucleotide" refers to DNA or RNA, for example as found in a living cell, with which the antisense molecule is intended to bind or react.

The term "polarity" as used herein refers to the orientation of a strand or linear molecule. For example, 5'→3' constitutes one polarity, while 3'→5' constitutes an opposite polarity. Not all linear molecules have an inherently defined polarity.

The term "flexible linker" refers to a moiety capable of covalently attaching a binding domain to a coupling moiety.

Suitable flexible linkers are typically linear molecules in a chain of at least one or two atoms, more typically an organic polymer chain of 1 to 12 carbon atoms (and/or other backbone atoms) in length. Exemplary flexible linkers include polyethylene glycol, polypropylene glycol, polyethylene, polypropylene, polyamides, polyesters, and the like.

The term "coupling moiety" as used herein refers to a reactive chemical group that is capable of reacting with another coupling moiety to join two molecules. The coupling moieties used in the invention should be able to bind in the absence of any target molecule, and are preferably selected such that the first coupling moiety reacts only with the second coupling moiety (under the conditions under which the library is prepared and used), and not with any other portion of the molecule or other first coupling moieties. Similarly, the second coupling moiety should react only with the first coupling moieties, and not with any other second coupling moiety (or any other portion of the molecules). Exemplary coupling moieties include complementary oligonucleotides (preferably selected such that they do not hybridize to any portion of the target polynucleotide), complementary oligonucleotide analogs (particularly employing bases which do not hybridize to natural bases), and electrophilic or nucleophilic moieties such as alkyl halides, alkyl sulfonates, activated esters, ketones, aldehydes, amines, hydrazines, sulfhydryls, alcohols, phosphates, thiophosphates, Michael addition receptors, dienophiles, dienes, dipolarophiles, nitriles, thiosemicarbazides, imidates, isocyanates, isothicyanates, alkynes, and alkenes. Where the antisense constructs comprise more than two component parts (for example, where three or four molecules are coupled to make the final construct), the coupling moieties are preferably selected such that the first and second coupling moieties react only with each other, and the third and fourth coupling moieties react only with each other, and so forth.

The term "stem" as used herein refers to the structure formed by coupling two oligonucleotide or oligonucleotide analog coupling moieties.

The term "activity" refers to the ability of an antisense molecule of the invention, when hybridized to a target polynucleotide, to interfere with the transcription and/or translation of the target polynucleotide. Preferably, the interference arises because the antisense molecule when hybridized serves to recruit a nuclease, and/or serves as a nuclease substrate. "Interference" includes inhibition to any detectable degree.

The term "hydrocarbyl" refers to a moiety consisting of carbon and hydrogen, and containing from one to about twelve carbon atoms. Exemplary hydrocarbyl groups include, without limitation, methyl, ethyl, propyl, butyl, 2-butyl, t-butyl, hexyl, and the like.

General Method

A preformed library of oligonucleotide analogs is provided, comprising a set of first oligonucleotide analogs and a set of second oligonucleotide analogs, the analogs having coupling moieties that provide for coupling each first oligonucleotide analog to a second oligonucleotide analog to form an antisense molecule. The oligonucleotide analogs are selected to act, when coupled, as a substrate for an endonuclease that recognizes double-stranded (ds) RNA or RNA/DNA hybrids when hybridized to a target nucleic acid. The binding domains need to be long enough to insure that the antisense molecule binds to the target polynucleotide, and is able to recruit and/or activate a nuclease. However, the number of molecules required for a complete library increases exponentially with the length of the sequence represented.

By conceptually separating the antisense molecules into two or more pieces, a comprehensive antisense library can be prepared in advance, rather than synthesizing a plurality of candidate antisense molecules as needed. A complete library of every possible 17 mer oligonucleotide, using the four natural bases, would consist of $4^{17}$ (or about $1.7 \times 10^{10}$) molecules. By providing the antisense molecules in at least two components, for example a library of 8 mers and a library of 9 mers, assembled quickly as needed, the size of the library needed is reduced to $4^8 + 4^9$, or 327,650 molecules. The required complexity of the library is still further reduced by substituting one or more universal or degenerate bases for some of the natural bases. Thus, for example, if the 9 mer library consists of 5 universal bases followed by 4 natural bases, the number of components drops to $4^4$ (256), and the total library size is reduced to $4^8 + 4^4$, about 66,000 molecules. The library complexity can also be reduced by dividing the antisense molecule into three or more segments. For example, a full 18 mer library would require $4^{18}$ molecules, or about $6.9 \times 10^{11}$ molecules. However, a library composed of first, second, and third hexamers that assemble to form 18 mers need only contain $4^6 + 4^6 + 4^6$, or 12,288 molecules, a size attainable with current parallel synthesis technology. If, for example, the middle hexamer set is replaced with a hexamer of universal bases, the library complexity is reduced by a third. It is possible to synthesize and maintain libraries of this size, and rapidly assemble any desired antisense molecule without the need for custom, de novo synthesis of long oligomers. Thus, one embodiment of the invention is a library comprising at least two sets of oligomers, wherein oligomers are selected from each set and coupled as needed.

The library size can be further reduced by avoiding certain sequences which are predicted to serve as poor antisense molecules by reason of poor binding ability, for example, AT-rich molecules; or artifact formation, for example, AG-rich regions, poly-C, $(GGN)_n$, $(GGGN)_n$, and TAT motifs.

FIG. 1 is a schematic illustration of an RNA-analog complex 100, having RNA 101 hybridized to an oligonucleotide analog comprising a first "anchor" domain 102 and a second "cleaver" domain 103 which hybridize to adjacent regions 110 and 111 of the RNA. The "cleaver" domain is also able to serve as a nuclease substrate. The first and second domains are connected to each other through first and second coupling moieties 106 and 107, which are linked to the first and second binding domains 102 and 103 by flexible linkers 104 and 105, respectively.

Figure 2:
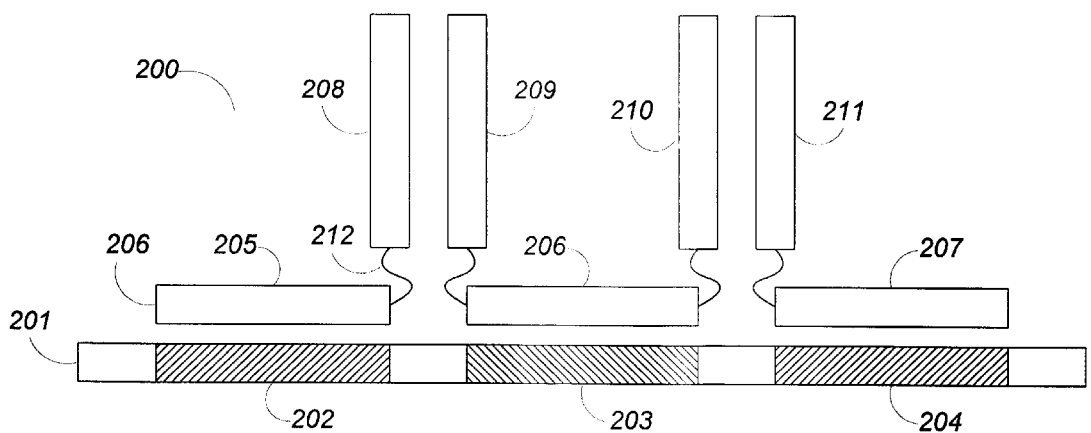
FIG. 2 schematically depicts an antisense construct having multiple oligomers.

FIG. 2 depicts an RNA-antisense molecule complex 200 having multiple oligomers. Binding domains 205, 206, 207 are coupled together by coupling moieties, here complementary oligonucleotides 208, 209, 210, 211 which are joined to the binding domains by flexible linkers 212. Target regions 202, 203, 204 can be adjacent, contiguous, or slightly spaced apart. The binding domains need not be of equal length.

At least one of the binding domains comprises about 3 to about 24 bases, preferably about 6 to about 8 bases. If desired, one domain may provide most of the target specificity, while the other domain primarily provides a nuclease substrate. For example, a library can be constructed having a set of 6 mer binding domains, each of which binds only a single 6 mer sequence, and a set of 8 mer binding domains, in which only four of the bases are sequence-specific, and the remaining bases are degenerate or universal. The first set contains a possible $4^6$ (4096) sequences (prior to eliminating undesirable sequences), while the second set contains only $4^4$ (256) sequences (prior to eliminating undesirable sequences, assuming 4 "specific" bases and 4 universal bases). By combining oligomers selected from the first and second sets as needed, one can generate $4^{10}$ ($10^6$) different sequences using only 4,352 molecules. In contrast, a complete library of 14 mers would require $4^{14}$ ($2.7 \times 10^8$) molecules.

The oligomers can be synthesized using standard oligonucleotide synthesis methods. For example, one can employ combinatorial synthesis techniques using pooling and splitting methods with AccuTag reactors (Irori, La Jolla, Calif.). Oligonucleotides can be synthesized on solid supports and stored, or cleaved into solution and stored until required. The oligonucleotides can be synthesized attached to solid supports by cleavable linkers. If desired, one can use linkers that can be cleaved under cell culture conditions (i.e., the linkers can be cleaved in the presence of cells without damaging the cells). Suitable linkers include photolabile linkers (Glen Research), linkers cleaved by β-elimination, oxidative cleavage, and enzymatic activity (for example, RNases, esterases, proteases and the like). This permits one to store and dispense the oligomers in a dry state, coupling them in situ.

The oligomer synthesis can be performed in the 3' to 5' direction for some library components, and the 5' to 3' direction for other components. In cases where the coupling moieties are oligonucleotides or oligonucleotide analogs, it is preferable to synthesize the coupling moiety last, so that synthesis failures result in molecules having an incomplete stem (and thus unable to couple).

The oligomers used in the binding domains can employ any backbone capable of resulting in a molecule that hybridizes to natural nucleic acids (DNA and/or RNA). Examples of suitable backbones include phosphodiesters and deoxy phosphodiesters, phosphorothioates and deoxy phosphorothioates, 2'-O-substituted phosphodiesters and deoxy analogs, 2'-O-substituted phosphorothioates and deoxy analogs, morpholino, peptide nucleic acids (Nielsen et al., U.S. Pat. No. 5,539,082), 2'-O-alkyl methylphosphonates, 3'-amidates, MMI, alkyl ethers (Cook et al., U.S. Pat. No. 5,223,618) and others as described in Cook et al., U.S. Pat. No. 5,378,825, Sanghvi et al., U.S. Pat. No. 5,489,677, Cook et al., U.S. Pat. No. 5,541,307, and the like. Where RNase activity is desired, a backbone capable of serving as an RNase substrate is employed for at least a portion of the oligomer.

Suitable bases include the following, without limitation:

| Nucleoside base | cleaver/anchor/stem | complexity (pairs with _) | Commercial? |
|---|---|---|---|
| deoxy adenosine | cleaver | normal | yes |
| deoxy guanosine | cleaver | normal | yes |
| deoxy cytidine | cleaver | normal | yes |
| thymidine | cleaver | normal | yes |
| deoxy diaminopurine | cleaver | normal, (U) | yes |
| deoxy propynyl C | cleaver | normal, (G) | yes |
| deoxy propynyl U | cleaver | normal, (A) | yes |
| deoxy 5-nitroindole | cleaver | universal | yes |
| deoxy P | cleaver | generic (A&G) | yes |
| deoxy K | cleaver | generic (U&C) | yes |
| deoxy 3-nitropyrrole | cleaver | universal | yes |
| deoxy 4-nitrobenzimidazole | cleaver | universal | |
| deoxy nebularine | cleaver | universal | yes |
| deoxy inosine | cleaver | universal | Yes |
| deoxy 2-aminopurine | cleaver | generic (U&C) | yes |
| 2'-OMe adenosine | anchor | normal | yes |
| 2'-OMe guanosine | anchor | normal | yes |
| 2'-OMe cytidine | anchor | normal | yes |
| 2'-OMe uridine | anchor | normal | yes |
| 2'-OMe diamino purine | anchor/stem | normal, (U) | yes |
| 2'-OMe inosine | anchor | universal | Yes |
| 2'-OMe 2-aminopurine | anchor | generic (U&C) | yes |
| 2'-OMe nebularine | anchor | universal | |
| 2'-OMe 5-nitroindole | anchor | universal | |
| 2'-OMe propynyl C | anchor/stem | normal | yes |
| 2'-OMe propynyl U | anchor/stem | normal | yes |
| 2'-OMe P | anchor | generic (G&A) | |
| 2'-OMe K | anchor | generic (U&C) | |
| 2'-OMe 4-nitrobenzimidazole | anchor | universal | |
| 2'-OMe 3-nitropyrrole | anchor | universal | |
| 2'-F adenosine | anchor | normal | yes |
| 2'-F guanosine | anchor | normal | yes |
| 2'-F cytidine | anchor | normal | yes |
| 2'-F uridine | anchor | normal | yes |
| 2'-F diaminopurine | anchor/stem | normal (U) | |
| 2'-F inosine | anchor | universal | |
| 2'-F-2-amino purine | anchor/stem | generic (U&C) | |
| 2'-F nebularine | anchor | universal | |
| 2'-F 5-nitroindole | anchor | universal | |
| 2'-F propynyl C | anchor/stem | normal | |
| 2'-F propynyl U | anchor/stem | normal | |
| 2'-F P | anchor | generic (G&A) | |
| 2'-F K | anchor | generic (U&C) | |
| 2'-F 4-nitrobenzimidazole | anchor | universal | |
| 2'-F 3-nitropyrrole | anchor | universal | |
| PNA-A | anchor/stem | normal | yes |
| PNA-G | anchor/stem | normal | yes |
| PNA-C | anchor/stem | normal | yes |
| PNA-T | anchor/stem | normal | yes |
| PNA-5-nitroindole | anchor | universal | |
| PNA propynyl C | anchor/stem | normal | |
| PNA-propynyl U | anchor/stem | normal | |
| PNA-2-aminopurine | anchor | generic (U&C) | |
| PNA-diaminopurine | anchor/stem | normal | |
| PNA-nebularine | anchor | universal | |
| PNA-inosine | anchor | universal | |
| PNA-P | anchor | generic (G&A) | |
| PNA-K | anchor | generic (U&C) | |
| PNA-4-nitrobenzimidazole | anchor | universal | |
| PNA-3-nitropyrrole | anchor | universal | |
| morpholino-A | anchor/stem | normal | yes |
| morpholino-G | anchor/stem | normal | yes |
| morpholino-C | anchor/stem | normal | yes |
| morpholino-U | anchor/stem | normal | yes |
| morpholino-5-nitroindole | anchor | universal | |
| morpholino-propynyl C | anchor/stem | normal | |
| morpholino-propynyl U | anchor/stem | normal | |
| morpholino-2-aminopurine | anchor | generic (U&C) | |
| morpholino-diaminopurine | anchor/stem | normal | |
| morpholino-nebularine | anchor | universal | |
| morpholino-inosine | anchor | universal | |
| morpholino-P | anchor | generic (G&A) | |
| morpholino-K | anchor | generic (U&C) | |
| morpholino-4-nitrobenzimidazole | anchor | universal | |
| morpholino-3-nitropyrrole | anchor | universal | |
| phosphoramidate-A | anchor/stem | normal | yes |
| phosphoramidate-C | anchor/stem | normal | yes |
| phosphoramidate-G | anchor/stem | normal | yes |
| phosphoramidate-U | anchor/stem | normal | yes |
| phosphoramidate-5-nitroindole | anchor | universal | |
| phosphoramidate-propynyl C | anchor/stem | normal | |
| phosphoramidate-propynyl U | anchor/stem | normal | |
| phosphoramidate-2-aminopurine | anchor | generic (C&U) | |

-continued

| Nucleoside base | cleaver/anchor/stem | complexity (pairs with _) | Commercial? |
|---|---|---|---|
| phosphoramidate-diaminopurine | anchor/stem | normal | |
| phosphoramidate-nebularine | anchor | universal | |
| phosphoramidate-inosine | anchor | universal | |
| phosphoramidate-P | anchor | generic (G&A) | |
| phosphoramidate-K | anchor | generic (U&C) | |
| phosphoramidate-4-nitrobenzimidazole | anchor | universal | |
| phosphoramidate-3-nitropyrrole | anchor | universal | |
| 2'-O-methoxyethyl adenosine | anchor | normal | |
| 2'-O-methoxyethyl guanosine | anchor | normal | |
| 2'-O-methoxyethyl cytidine | anchor | normal | |
| 2'-O-methoxyethyl uridine | anchor | normal | |
| 2'-O-methoxyethyl diaminopurine | anchor/stem | normal (U) | |
| 2'-O-methoxyethyl inosine | anchor | universal | |
| 2'-O-methoxyethyl 2-aminopurine | anchor | generic (U&C) | |
| 2'-O-methoxyethyl nebularine | anchor | universal | |
| 2'-O-methoxyethyl 5-nitroindole | anchor | universal | |
| 2'-O-methoxyethyl propynyl C | anchor/stem | normal | |
| 2'-O-methoxyethyl propynyl U | anchor/stem | normal | |
| 2'-O-methoxyethyl P | anchor | generic (G&A) | |
| 2'-O-methoxyethyl K | anchor | generic (U&C) | |
| 2'-O-methoxyethyl 4-nitro-benzimidazole | anchor | universal | |
| 2'-O-methoxyethyl 3-nitropyrrole | anchor | universal | |
| deoxy Rp MP-AG dimer | anchor/stem | normal | |
| deoxy Rp MP-GA dimer | anchor/stem | normal | |
| deoxy Rp MP-AC dimer | anchor/stem | normal | |
| deoxy Rp MP-CA dimer | anchor/stem | normal | |
| deoxy Rp MP-AT dimer | anchor/stem | normal | |
| deoxy Rp MP-TA dimer | anchor/stem | normal | |
| deoxy Rp MP-AA dimer | anchor/stem | normal | |
| deoxy Rp MP-GG dimer | anchor/stem | normal | |
| deoxy Rp MP-CC dimer | anchor/stem | normal | |
| deoxy Rp MP-TT dimer | anchor/stem | normal | |
| deoxy Rp MP-GC dimer | anchor/stem | normal | |
| deoxy Rp MP-CG dimer | anchor/stem | normal | |
| deoxy Rp MP-GT dimer | anchor/stem | normal | |
| deoxy Rp MP-TG dimer | anchor/stem | normal | |
| deoxy Rp MP-CT dimer | anchor/stem | normal | |
| deoxy Rp MP-TC dimer | anchor/stem | normal | |
| deoxy Rp MP-5-nitro-indole dimer | anchor | universal | |
| deoxy Rp MP-KP dimer | anchor | generic | |
| deoxy Rp MP-PK dimer | anchor | generic | |
| deoxy Rp MP-KK dimer | anchor | generic | |
| deoxy Rp MP-PP dimer | anchor | generic | |
| 2'-OMe Rp MP-AG dimer | anchor/stem | normal | |
| 2'-OMe Rp MP-GA dimer | anchor/stem | normal | |
| 2'-OMe Rp MP-AC dimer | anchor/stem | normal | |
| 2'-OMe Rp MP-CA dimer | anchor/stem | normal | |
| 2'-OMe Rp MP-AT dimer | anchor/stem | normal | |
| 2'-OMe Rp MP-TA dimer | anchor/stem | normal | |
| 2'-OMe Rp MP-AA dimer | anchor/stem | normal | |
| 2'-OMe Rp MP-GG dimer | anchor/stem | normal | |
| 2'-OMe Rp MP-CC dimer | anchor/stem | normal | |
| 2'-OMe Rp MP-TT dimer | anchor/stem | normal | |
| 2'-OMe Rp MP-GC dimer | anchor/stem | normal | |
| 2'-OMe Rp MP-CG dimer | anchor/stem | normal | |
| 2'-OMe Rp MP-GT dimer | anchor/stem | normal | |
| 2'-OMe Rp MP-TG dimer | anchor/stem | normal | |
| 2'-OMe Rp MP-CT dimer | anchor/stem | normal | |
| 2'-OMe Rp MP-TC dimer | anchor/stem | normal | |
| 2'-OMe Rp MP-5-nitroindole dimer | anchor | universal | |
| 2'-OMe Rp MP-KP dimer | anchor | generic | |
| 2'-OMe Rp MP-PK dimer | anchor | generic | |
| 2'-OMe Rp MP-KK dimer | anchor | generic | |
| 2'-OMe Rp MP-PP dimer | anchor | generic | |
| RiboPyranoysl A | stem | self/normal | |
| RiboPyranoysl G | stem | self/normal | |
| RiboPyranoysl C | stem | self/normal | |
| RiboPyranoysl U | stem | self/normal | |
| MMI-AG dimer | anchor/stem | normal | |
| MMI-GA dimer | anchor/stem | normal | |
| MMI-AC dimer | anchor/stem | normal | |
| MMI-CA dimer | anchor/stem | normal | |
| MMI-AT dimer | anchor/stem | normal | |
| MMI-TA dimer | anchor/stem | normal | |
| MMI-AA dimer | anchor/stem | normal | |
| MMI-CC dimer | anchor/stem | normal | |
| MMI-GG dimer | anchor/stem | normal | |
| MMI-TT dimer | anchor/stem | normal | |
| MMI-GC dimer | anchor/stem | normal | |
| MMI-CG dimer | anchor/stem | normal | |
| MMI-GT dimer | anchor/stem | normal | |
| MMI-TG dimer | anchor/stem | normal | |
| MMI-CT dimer | anchor/stem | normal | |
| MMI-TC dimer | anchor/stem | normal | |

The coupling moieties are selected to join two oligomers from different sets by either covalent or non-covalent interaction, for example a non-covalent binding pair. The coupling moieties are preferably selected such that the coupling moiety present on oligomers of one set in a library do not couple with each other, but bind readily with coupling moieties on oligomers of the another set, thus insuring that the oligomers couple in the intended orientation. In one embodiment, the coupling moieties are complementary oligonucleotides. The complementary regions can be separated by several non-complementary bases, to provide an inherent flexible linker. The complementary oligonucleotides can be attached to the binding domains in the same polarity or orientation, or can be provided in reverse polarity or orientation. For example, where the binding domain is in the 5'-3' orientation, the complementary oligonucleotide coupling moiety can be attached in the 3'-5' orientation, thus reducing the chances that the coupling moiety will inadvertently participate (or interfere with) binding to the target polynucleotide. In another embodiment, the oligonucleotide comprises unnatural bases which do not hybridize with natural bases.

The coupling moieties may also join as the result of covalent chemical interactions, for example, by condensation, cycloaddition, or nucleophilic-electrophilic addition. In one embodiment, one coupling moiety can be a sulfhydryl group, while its complementary coupling moiety is a succinimidyl group. In another embodiment, one coupling moiety is an amine or a hydrazine moiety, while the complementary coupling moiety is a carbonyl group (aldehyde, ketone, or activated ester). In another embodiment, one coupling moiety is a maleimidyl group while the complementary coupling moiety is a sulfhydryl group. In another embodiment, one coupling moiety is an aryl-dihydroxyboron group which binds to adjacent OH groups on ribose.

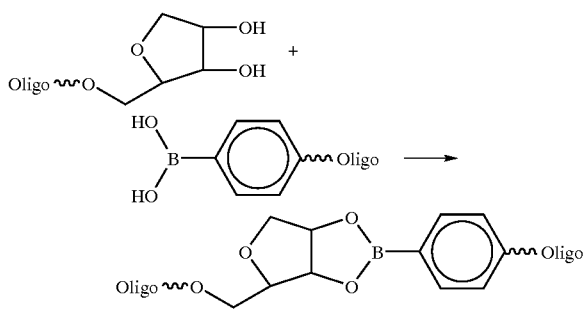

In another embodiment, an oxazole derivative forms one coupling moiety, while its complement comprises a diketotriazole, as described by T. Ibata et al., *Bull Chem Soc Japan* (1992) 65:2998–3007:

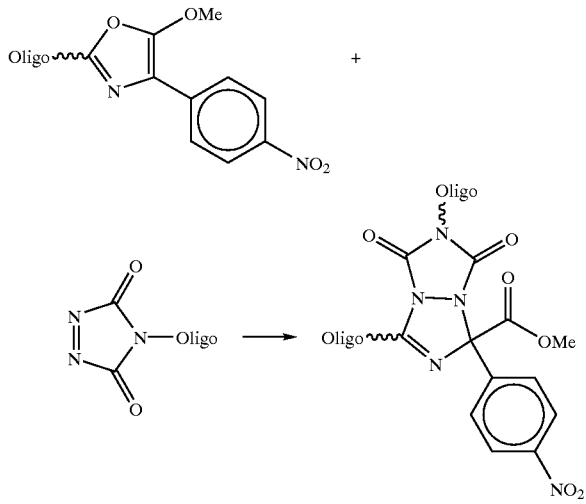

In libraries with more than two sets of oligomers (i.e., where the antisense molecule comprises three or more oligomers coupled together), the coupling moieties can be selected to be orthogonal to each other to insure that the oligomers are assembled in the intended order. For example, the coupling moieties between the first and second oligomers can be sulfhydryl and maleimide groups, while the coupling moieties between the second and third oligomers can be diene and dienophile groups. Suitable coupling moieties include, without limitation, alkyl halides, alkyl sulfonates, activated esters, ketones, aldehydes, amines, hydrazines, sulfhydryls, alcohols, phosphates, thiophosphates, Michael addition receptors, dienophiles, dienes, dipolarophiles, nitriles, alkynes, thiosemicarbazides, isothiocyanates, isocyanates, imidates, and alkenes.

Flexible linkers are optionally used to relieve stress that might otherwise result from interposing the coupling moieties between two binding domains that bind to adjacent regions of target nucleic acid. The flexible linker is preferably selected to be flexible, hydrophilic, and of sufficient length that the bulk of the coupling moieties does not interfere with hybridization, RNase recognition, and/or RNase activity on the complex. It is preferred, but not essential, to employ a flexible linker between each binding domain and its coupling moiety. It is preferred to employ a linker at least between the binding domain and coupling moiety that serves as an RNase substrate, and more preferred to employ flexible linkers in each oligomer. The linker may be connected to the terminal base of the binding domain, or can be connected one or more bases from the end. Suitable flexible linkers are typically linear molecules in a chain of at least one or two atoms, more typically an organic polymer chain of 1 to 12 carbon atoms (and/or other backbone atoms) in length. Flexible linkers also include additional bases, not complementary to the target sequence. Exemplary flexible linkers include polyethylene glycol, polypropylene glycol, polyethylene, polypropylene, polyamides, polyesters, and the like.

The individual oligomers can be assembled in vitro or in vivo. The coupling moieties are preferably selected to join spontaneously, under the conditions of the intracellular environment. Thus, one can administer separate oligomers individually, for agent formation in vivo. Alternatively, one can join oligomers in vitro prior to administration. One can further employ transfection aids to increase the rate of uptake, for example Lipofectin, Lipofectamine, Lipofectace, and the like.

The activity of various constructs of the invention can be determined by standard assay methods, for example as set forth in the Examples below. In general, one can prepare a target polynucleotide having a known sequence, contact the target with oligomers of the invention selected to bind the target sequence to form a complex, subject the complex to cleavage with the desired target nuclease, and analyze the products to determine if cleavage occurred.

The library of the invention can be prepared in advance. If a sequence for a target polynucleotide is supplied, oligomers corresponding to the sequence are selected from the library, combined to form a plurality of antisense agents, and the agents applied to a plurality of test cells that express the target. The agents can be applied individually or in mixtures. Activity can be determined by detecting cleaved target polynucleotides directly (e.g., by hybridization to a labeled probe, amplification with PCR, visualization on a gel, and the like), or by an effect on the host cell phenotype (for example, expression or lack of expression of a selected protein).

Alternatively, where the target sequence is unknown, one can assemble a plurality of agents and determine empirically which sequences result in active agents. For example, assume a protein of unknown sequence expressed by a known cell. One can provide a plurality of antisense molecules of the invention consisting of every combination of oligomers in each set in the library, e.g.,

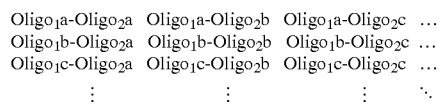

As there may be too many antisense molecules to investigate each combination individually, it may be preferable to pool the antisense molecules for testing. For example, if the first set contains about 4,000 hexamer sequences (all bases non-degenerate and non-universal), and the second set contains about 250 octamer sequences (having 4 universal bases and 4 specific bases), the complete library would contain about $10^6$ individual combinations. These molecules can be pooled easily, for example by coupling each individual octamer sequence to a mixture of all hexamer sequences, resulting in 250 pools of 4,000 combinations. Each pool is then tested against cells known to express the unidentified protein, and pools that result in modulation of the protein expression are identified. The active pools can be further subdivided (for example, by coupling the "active" octamer with 200 individual mixtures of hexamer, to form 200 pools of 200 combinations) and tested iteratively until the active antisense molecule is identified, or examined by other means.

The oligomers and methods of the invention can also be applied to generate ribozymes, and libraries of ribozymes. The minimum sequence requirement for ribozyme activity are described by F. Benseler et al., *J Am Chem Soc* (1993) 115:8483–84, incorporated herein by reference. Hammerhead ribozyme molecules comprise end domains ("I" and "III") which hybridize to the substrate polynucleotide, a catalytic portion, and a stem loop structure ("II") which can be substituted by a variety of other structures capable of holding the molecule together. These molecules can be assembled from oligomers of the invention, replacing the II domain stem loop with coupling moieties as described above. Thus, for example, one can prepare a library of oligomers having as the first set a plurality of oligonucleotides or oligonucleotide analogs having the sequence 5'-GGNNNNNCUGAUGA-$cp_1$ (SEQ ID NO: 1) (domain I, first portion of catalytic moiety, and first coupling moiety), and as the second set a plurality of oligonucleotides or oligonucleotide analogs having the sequence 5'-cp2-GAANNNNN (SEQ ID NO:2) (second coupling moiety, second portion of catalytic moiety, and domain III), where the bases "N" are selected to hybridize to the target substrate. These ribozymes can be assembled in advance, for determining the optimum cleavage site of a target polynucleotide of known sequence, or can be assembled in a combinatorial fashion as described above, to determine effective molecules for inhibiting a target of unknown sequence.

EXAMPLES

The following examples are provided as a guide for those skilled in the art, and are not to be construed as limiting the invention in any way. All products are used according to manufacturer's instructions, and experiments are conducted under standard conditions, unless otherwise specified.

All reagents are dry (<30 ppm water). DNA synthesis reagents (oxidizer, tetrazole, capping reagents, propyl linker support, 2'-deoxy, 2'-OMe, and spacer 9 amidites) were purchased from Glen Research (Sterling, Va.). Amidites in solution are dried over Trap-paks from Perseptive Biosystems. Protected amino acids, PyBOP, and chlorotritylchloride resin were obtained from NovaBiochem.

Example 1

Cleaver Synthesis-Hybridization Motif (A) A solid support that was previously derivatized with a dimethoxy trityl group (DMT) protected propyl linker was placed in a DNA synthesizer column compatible with a Perseptive Expedite synthesizer (1 μmole of starting propyl linker). The DMT group was removed with a deblock reagent (2.5% dichloroacetic acid in dichloromethane (DCM)). The standard protocols for RNA synthesis were applied to 2'-OMe β-cyanoethyl amidites (0.1 M in dry acetonitrile). The amidites were activated with tetrazole (0.45 M in dry acetonitrile). Coupling times were typically up to 15 minutes for 2'-OMe amidites. To synthesize the stem portion of the cleaver oligonucleotides, the 2'-OMe phosphonite intermediate was treated with an oxidizer (0.02 M iodine in THF/pyridine/water 68/20/2). After each oxidation step, a capping step which placed an acetyl group on any remaining uncoupled 5'-OH groups was introduced by treatment with a mixture of two capping reagents (CAP A=acetic anhydride in THF, and CAP B=N-methylimidazole in THF). The cycle was repeated 15 times with various amidites to obtain the desired sequence. Spacer 9 (Glen Research, cat# 10-1909-90) was introduced using manual coupling protocols. Spacer 9 was coupled twice to ensure proper coupling. Manual coupling was done by attaching the column containing the support with the first part of the oligonucleotide to a syringe containing deblock solution. Solution was passed until all orange color disappeared. The column was washed with dry acetonitrile (3×10 ml). One syringe containing 100 μl of activator was attached to one end of the column and another syringe containing 100 μl of the amidite (0.1 M solution) was attached to the other end of the column. The syringes were plunged alternately to drive the mixture of activator and amidite back and forth over the support. The procedure for coupling the amidite was repeated. The support was then washed with acetonitrile (10 ml) and the support treated with oxidizer solution (3 ml). The support was then washed again with acetonitrile (10 ml) and capping solution (an equal mixture of cap A and cap B, freshly mixed) was passed over the support. The support was washed with dry acetonitrile (10 ml). The trityl group of the spacer 9 was removed with deblock solution, and the support washed with acetonitrile (10 ml) before placing the column on the synthesizer. A segment of deoxy-phosphorothioate was then synthesized. This was done by coupling 2'-deoxy-β-cyanoethyl phosphoramidites to the spacer 9 linker. The standard coupling cycle of the Expedite was used. The exception to the cycle described above for 2'-OMe was that coupling times were typically shorter and Beaucage sulfurizing reagent (Glen Research, cat.# 40-4036-10) was used instead of iodine oxidizer to give the phosphorothioate internucleotide linkage. The trityl group was allowed to remain on the last base. The support was treated at 55° in concentrated $NH_4OH$ for 16 hours. The solution was concentrated on a speed vac and the residue taken up in 100 μl aqueous 0.1 M triethyl ammonium acetate ("TEAA"). This was applied to an HPLC column (C-18, Kromasil, 5 μm, 4.3 mm diameter, 250 mm length) and eluted with a $CH_3CN$ gradient (solvent A: 0.1 M TEAA, solvent B: 0.1 M TEAA and 50% acetonitrile) over 30 minutes at 1 ml/min. flow rate. Fractions of greater than 80% pure product were pooled and concentrated. The resulting residue was taken up in 80% acetic acid in water to remove the trityl group and reapplied to a reverse phase column and purified as described above. Fractions containing greater than 90% purity were pooled and concentrated.

(B) Oligonucleotides useful for recruiting RNase L are prepared as in part (A) above, substituting 2'-OMe phosphoramidites for the deoxy amidites used after spacer 9. The resulting oligo has a 2'-OMe diester portion at the 3' side of the spacer, and a 2'-OMe phosphorothioate on the 5' side of the spacer. A linker attached to oligo 2'–5' adenosine is attached to the 5' end of the oligo as described by Torrence et al., U.S. Pat. Nos. 5,583,032, and 5,677,289, both incorporated herein by reference. The product is purified as described by Torrence et al.

(C) Rhodamine Labelled Cleaver: A rhodamine labelled cleaver was synthesized as in part (A) above, except that the trityl group was removed from the last base and to that base was coupled a protected amine linker (Perkin-Elmer cat. # 402872). The deprotection of the oligonucleotide was performed as described in part (A) above. The oligonucleotide was taken up in 10 M $NH_4OAc$ and EtOH added to make a 70% ethanolic solution to precipitate the oligonucleotide. The oligonucleotide was pelleted, and the pellet taken up in 100 mM $NaHCO_3$. The isothiocyanate derivative of rhodamine (Molecular Probes cat. # X-491) was added and the mixture allowed to stir for 4 hours. The mixture was purified as described in part (A) above.

Example 2

Anchor Synthesis-Hybridization Motif (A) An oligonucleotide was prepared as described in Example 1(A) above, except that the 2'-OMe amidites that are added before the spacer ("9") (synthesizing 3'–5') are oxidized with Beaucage reagent to form phosphorothioate linkages. 2'-OMe amidites are used after the spacer 9 linkage and are oxidized with the iodine oxidizer to give phosphodiester linkages. The resulting oligonucleotide was purified as in Example 1.

(B) Fluroescein Labelled Anchor: A fluorescein-labelled anchor was synthesized as in part (A) above, except that the trityl group was removed from the last base and to that base was coupled a protected amine linker (Perkin-Elmer cat. # 402872). The deprotection of the oligonucleotide was done as described in part (A). The oligonucleotide was taken up in 10 M $NH_4OAc$ and EtOH added to make a 70% ethanolic solution to precipitate the oligonucleotide. The oligonucleotide was pellet was taken up in 100 mM $NaHCO_3$. The isothiocyanate derivative of fluorescein (Molecular Probes cat. # F-1907) was added and the mixture allowd to stir for 4 hours. The mixture was purified as described in part (A).

Example 3

Cleavers with Pyranosyl RNA Stems

Cleaver oligonucleotides were prepared as described in Example 1 above, but substituting pyranosyl RNA monomers for the 2-OMe β-cyanoethyl amidites. Synthesis and deprotection conditions were used as described by Pitsch et al., *Helv Chimica Acta* (1993) 76:2161–2183.

Example 4

Anchors with Pyranosyl RNA Stems

Anchor oligonucleotides were prepared as described in Example 2 above, but substituting pyranosyl RNA monomers and synthesis conditions after the spacer 9 linker for the 2'-OMe monomers and phosphodiester synthesis conditions. Purification was as described in Example 2.

Example 5

Cleaver Synthesis-Hybridization Motif

Histidine 6 Synthesis: To a suspension of 2-chlorotritylchloride resin in dry $CH_2Cl_2$ (DCM) was added N-α-Fmoc-N-π-t-butoxymethyl-L-histidine (0.6 eq, Fmoc-His(Bum)-OH) with sufficient dimethylacetamide to provide solubility. Diisopropylamine (4 eq) was added, and the mixture stirred strongly for 30 min. The product was filtered, and the resin washed with 3×DCM/MeOH/DIPEA) (17:2:1), followed by 3 DCM washes, 2 DMF washes, 2 more DCM washes, and finally 2 MeOH washes. The resin was dried in vacuo over KOH to remove excess MeOH. Loading of histidine was determined spectrophotometrically by release of Fmoc with 20% piperidine in DMF. The first Fmoc was removed by treating the Fmoc-histidine resin with 5% piperidine in DCM/DMA (1:1) for 10 min, followed by 20% piperidine in DMA for 15 min. The free amine was treated with Fmoc-His(Bum)-OH (2.5 eq), PyBOP (2.5 eq), and DIPEA (5 eq) in DMA. Coupling was allowed to proceed for 30 min, after which the resin was filtered and washed with DMA. The Fmoc was removed again with 20% piperidine in DMA, and the coupling cycle repeated three more times to provide a resin-bound His hexamer. The hexamer was removed from the resin and the Bum protecting groups removed with 95% aqueous trifluoroacetic acid. The product was purified by RP-HPLC (Kromasil C18, 5 μm, 4.3 mm diameter, 250 mm length) with a gradient from solvent A to solvent B of 50 min (A: 0.1% $TFA/H_2O$; B: $CH_3CN/H_2O/TFA$ 90/10/0.1). Fractions of >90% purity were pooled and concentrated by speed vac. The structure was confirmed by positive ion mass spectroscopy [M+H] 802.

Synthesis of Z-ACPID: Z-(amino-1-carboxypentyl) iminodiacetic acid (Z-ACPID) was synthesized according to the procedure of Hochuli et al., *J Chromatog* (1987) 411:177–84.

Synthesis of ACPID: A suspension of Z-protected NTA (2.0 g) in 1:3 $H_2O$:EtOH was heated until the mixture became clear. To this was added 10% Pd/C (2.0 g) and 20 ml of cyclohexene. The mixture was heated at reflux for 2 hours. The Pd/C was filtered, and the filtrate reduced in vacuo to give a solid foam. The structure was confirmed by negative ion mass spectroscopy [M–H] 261. Yield was 900 mg.

ACPID Derivatized Cleaver: A solid support that was previously derivatized with a dimethoxy trityl group (DMT) protected propyl linker is placed in a DNA synthesizer column compatible with a Perseptive Expedite synthesizer (1 μmole of starting propyl linker). The DMT group is removed with a deblock reagent (2.5% dichloroacetic acid in dichloromethane). The standard protocols for DNA synthesis are applied to 3'0-DMT-5'-O-β-cyanoethyl amidites (0.1 M in dry acetonitrile, <30 ppm $H_2O$). The amidites are activated with tetrazole (0.45 M in dry acetonitrile, <30 ppm $H_2O$). The phosphonite intermediate is treated with Beaucage reagent to form the phosphorothioate linkage. After each oxidation step a capping step which places an acetyl group on any remaining uncoupled 3'-OH groups is introduced by treatment with a mixture of two capping reagents (CAP A:acetic anhydride in THF and CAP B:N-methylimidazole in THF). The cycle is repeated 12 times with various bases to obtain the desired sequence. To the last 3'-OH is coupled a thiol-modifier (thiol modifier C6 S-S, Glen Research 10-1936) that puts a protected disulfide on the oligonucleotide. The DMT is removed with DCA. The support is treated with excess tris-carboxyethyl phosphine (TCEP, Pierce cat. # 20490) and washed to remove the excess TCEP. The resulting sulfhydryl is treated with excess succinimidyl 4-(p-maleimidophenyl)butyrate (SMPB, Pierce cat. # 22315). The support is washed to remove excess SMPB. The resulting NHS ester is reacted with excess ACPID ((amino-1-carboxypentyl)iminodiacetic acid). The resulting metal chelating oligonucleotide conjugate is then washed to remove excess ACPID. The support is treated at 55° C. in concentrated ammonium hydroxide for 16 hours. The solution is concentrated on a speed vac and the residue taken up in 100 μl aqueous 0.1 M triethyl ammonium acetate. This is applied to an HPLC column (C-18, Kromasil, 5 μm, 4.3 mm diameter, 250 mm length) and eluted with an acetonitrile gradient (solvent A: 0.1 M TEAA; solvent B: 0.1 M TEAA and 50% acetonitrile) over 30 minutes at 1 ml/min. flow rate. Fractions of greater than 90% purity are pooled and concentrated.

His 6 Derivatized Anchor: A solid support that was previously derivatized with a dimethoxy trityl group (DMT) protected propyl linker is placed in a DNA synthesizer column compatible with a Perseptive Expedite synthesizer (1 μmole of starting propyl linker). The DMT group is removed with a deblock reagent (2.5% dichloroacetic acid in dichloromethane). The standard protocols for RNA synthesis are applied to 5-O-DMT-2'-OMe-3'-O-β-cyanoethyl amidites (0.1 M concentration in dry acetonitrile, <30 ppm $H_2O$). The amidites are activated with tetrazole (0.45 M in dry acetonitrile, <30 ppm H2O). Coupling times are typically up to 15 minutes for 2'-OMe amidites. The phosphonite intermediate is treated with Beaucage reagent to form the phosphorothioate linkage. After each oxidation step, a capping step which places an acetyl group on any remaining uncoupled 5'-OH groups is introduced by treatment with a mixture of two capping reagents (CAP A:acetic anhydride in THF, and CAP B:n-methylimidazole in THF). The cycle is repeated 8 times with various bases to obtain the desired sequence. To the last 3'-OH is coupled a thiol-modifier (thiol modifier C6 S-S, Glen Research 10-1936) that puts a protected disulfide on the oligonucleotide. The DMT is removed with DCA. The support is treated with excess tris-carboxyethyl phosphine (TCEP, Pierce cat. # 20490) and washed to remove the excess TCEP. The resulting sulfhydryl is treated with excess succinimidyl 4-(p-maleimidophenyl) butyrate (SMPB, Pierce cat. # 22315). The support is washed to remove excess SMPB. The resulting NHS ester is reacted with excess histidine hexamer. The resulting oligohistidine oligonucleotide conjugate is then washed to remove excess histidine hexamer. The support is treated at 55° C. in concentrated ammonium hydroxide for 16 hours. The solution is concentrated on a speed vac and the residue taken up in 100 μl of aqueous 0.1 M triethyl ammonium acetate. This is applied to an HPLC column (C-18, Kromasil, 5 μm, 4.3 mm diameter, 250 mm length) and eluted with an acetonitrile gradient (solvent A: 0.1 M TEAA; solvent B: 0.1 M TEAA and 50% acetonitrile) over 30 minutes at 1 ml/min. flow rate. Fractions of greater than 90% purity are pooled and concentrated.

His 6 Derivatized Cleaver: The oligonucleotide is synthesized in the same fashion as the ACPID cleaver described above, except that a histidine hexamer is used to conjugate to the NHS ester instead of ACPID.

ACPID Derivatized Anchor: The oligonucleotide is synthesized in the same fashion as the Histidine 6 anchor described above except that the ACPID molecule is used to conjugate to the NHS ester instead of histidine hexamer.

Linking ACPID anchor oligonucleotide to His 6 cleaver oligonucleotide: The ACPID anchor oligonucleotide is treated with 10 eq of a 0.1 N solution of $NiSO_4$. The mixture was passed through a G-25 gel filtration spin column to remove the excess nickel. A solution of the His6 cleaver is added to the nickel charged ACPID anchor oligonucleotide. The linkage of the anchor and cleaver through the his6 nickel chelate is confirmed on polyacrylamide gel (19%).

Linking ACPID cleaver oligonucleotide to His 6 anchor oligonucleotide: The ACPID cleaver oligonucleotide is treated with 10 equivalents of a 0.1 N solution of $NiSO_4$. The mixture was passed through a G-25 gel filtration spin column to remove the excess nickel. A solution of the His6 anchor is added to the nickel charged ACPID anchor oligonucleotide. The linkage of the anchor and cleaver through the His6 nickel chelate is confirmed on polyacrylamide gel (19%).

Synthesis of cleavers containing universal bases: Oligonucleotides containing universal bases (5-nitroindole, inosine) were synthesized as described in Example 1 above, substituting the modified monomers for natural bases.

Example 6

Assay

Materials: Polymerase chain reaction (PCR) was used to prepare a dsDNA fragment encoding part of secreted alkaline phosphatase (SEAP) using the following primers:
P3 (SEQ ID NO:3) 5'-cgaaattaaatcgactcactat-3'
P3.1 (SEQ ID NO:4) 3'-gctttaattatgctgagtgatatcccgaagct-
  tagcgct taagcgggtggtacgacgacgacgacgacgacgacccggac-5'
P4 (SEQ ID NO:5) 3'-tagggtcaactcctcctcttgg-5'
P5 (SEQ ID NO:6) 3'-tacgacgacgacgacgacgacgacccggact-
  ccgatgtcgagagggacccgtagtagggtcaactcctcctcttgg-5'

These primers are based on the SEAP RNA fragment (1 to 102) having the sequence (SEQ ID NO:7) 5'-gggcttcgaatcgcgaattcgcccaccatgctgctgctgctgctgctgctggg-cctgaggctacagctctccctgggcatcatcccagttgaggaggagaacc The PCR amplification was performed under the manufacturer's (Life Technologies, Cat. No. 10198-018) recommended reaction conditions. Primers P3.1 and P5 were used at 10 nM, while primers P3 and P4 were used at 0.50 μM. The PCR program was 94° C. for 5 minutes, 35 cycles of 52° C. for 30 seconds, 72° C. for 1 minute, 94° C. for 45 seconds, then 72° C. for 10 minutes.

SEAP dsDNA was then transcribed into ssRNA using a RiboMax™ large Scale RNA kit (Promega, Cat. No. P1300). The SEAP DNA concentration was 30 μg/mL. The transcription reaction was terminated by adding DNase I and incubating at 37° C. for 15 minutes. DNA fragments and free nucleotides were removed by precipitation in EtOH/NaOAc and washing with 70% EtOH. The RNA was resuspended and diluted to approximately 2 μM for use in the RNase H activity assays.

Assay: Test oligonucleotides (20 μM each), SEAP RNA (10 μl of 2 μM solution), and Tris/EDTA buffer (10 mM Tris-HCl, pH 7.4, 1 mM EDTA, "TE", qs to 2 μl) were added to 500 μl thin-wall reaction tubes and incubated for 3 to 5 minutes at 40° C. to reach thermal equilibrium. RNase H buffer (10×: 200 mM Tris-HCl, pH 7.4–7.5, 1000 mM KCl, 100 mM $MgCl_2.6H_2O$, 0.5 mM DTT, 25% w/v sucrose), RNase H (0.4 to 0.6 U, Promega, Cat. No. M4281), and water (qs to 20 μL), were combined to form a cocktail, and incubated for 3 to 5 minutes at 40° C. Then, 8 μl of the cocktail was added to each reaction tube and mixed as quickly as possible to prevent cooling. Reactions were incubated at 40° C. for 30 minutes in an MJ Research PCT-100 temperature controller. Reactions were stopped by adding 20 μl FDE sample buffer (90% v/v formamide, 10% v/v 10× TBE buffer, 0.5% w/v bromophenol blue, 25 mM EDTA) (1× TBE: 89 mM Tris base, 89 mM boric acid, 2 mM EDTA, pH 8.0) to each reaction and heating to 90° C. for 3 to 5 minutes.

Detection: Each sample (8 to 10 μl) was run on denaturing 15% polyacrylamide gels at 200 volts for about one hour, or until the dye front had reached the bottom of the gel. Gels were run in electrophoresis cassettes, 8 cm×8 cm×1 mm (Novex, Cat. No. NC2010). Gels were poured immediately before use. Briefly, unpolymerized denaturing gel mix (10 ml) was degassed thoroughly under vacuum, combined with 10% ammonium persulphate (35 µl, BioRad) and TEMED (12 µl, BioRad), and poured into each cassette. After polymerization, gels were pre-electrophoresed at 250–300 volts until the current had stabilized at 4 to 5 mA per gel.

Nucleic acid bands in gels were visualized by soaking the gels in a 1:10,000 dilution of CyberGold™ (Molecular Probes, Cat. No. S-11494) in 1× TBE for 5 to 10 minutes, soaking in 1× TBE for an additional 5–10 minutes, and irradiating on a short wave UV transilluminator. The results were recorded by photographing the CyberGold™ fluorescence using a CyberGREEN™ filter and a Polaroid MP-4 camera with Polaroid Type 667 3000 ASA black and white film.

Duplex DNA ladders (20 bp and 100 bp, GenSura, San Diego) were used as size standards. Standard ladders were not heated before loading on gels, and were undenatured, running as duplex DNA fragments in both denaturing and non-denaturing gels.

Band Shifts: Gel band shifts were performed with anchor/cleaver pairs in order to demonstrate the high affinity of the oligonucleotides for each other in the absence of the RNA target.

Various anchor and cleaver oligonucleotides were mixed together in 1× RNase H buffer, 15% glycerol, and 6% FDE, and heated to 65° C. for 30 seconds. The final concentration of each oligonucleotide was 6.6 µM. After cooling to room temperature, the samples were run directly on a non-denaturing 15% (19:1) acrylamide gel containing 1 M urea and 1× TBE. Non-denaturing gels for band shift experiments were prepared, run, and visualized the same way as denaturing gels, substituting non-denaturing gel mix for denaturing gel mix.

Complementary cleaver/anchor duplexes containing fluorescently tagged oligonucleotides 1015 and 1016 (1015=rhodamine, 1016=fluorescein, and pairs 1000/1016, 1015/1010, 1015/1012, 1015/1013, 1015/1014, and 1015/1016) were demonstrated to hybridize efficiently to each other in the absence of target RNA by gel shift analysis under non-denaturing, stringent conditions. The components are set forth in Table 1. Duplex formation was confirmed by a strong mobility shift in the gel compared to size standards.

where "ACGT" indicates PS DNA, "ACGT" indicates 2'-OMe RNA, "acgt" indicates 2'-OMe PS RNA, and "9" indicates Glen Research linker #9.

TABLE 2 duplex formation in the absence of target RNA

| Cleaver/Anchor | Relative Mobility, denaturing conditions | Relative Mobility of Complex, non-denaturing conditions |
|---|---|---|
| 1015 | 25 | 25 |
| 1015/1010 | 25/27 | 44 |
| 1015/1012 | 25/23 | 39 |
| 1015/1013 | 25/21 | 37 |
| 1015/1014 | 25/19 | 35 |
| 1016 | 25 | 25 |
| 1016/1000 | 25/27 | 41 |
| 1016/1015 | 25/25 | 39 |

Gels were photographed before and after CyberGold staining to visualize the fluorescently labeled oligonucleotides (1015 and 1016) alone, and in complexes with unlabled oligonucleotides. Both photographs were identical except for the DNA standard ladders revealed by the CyberGold fluorescence.

Melting Point Determination: The melting point of the 15 base 2'-O-methyl RNA duplex stem used to bring the cleavers and anchors together was determined by UV spectroscopy. A Carey 3E (Varian) spectrophotometer with a thermal controller was used to monitor the absorbance of anchor/cleaver pairs 1000/1010 and 1000/1013 in MP buffer (150 mM NaCl, 10 mM $Na_2HPO_4$, 0.1 mM EDTA, pH 7.4).

An increase in absorbance of 0.1 AU at 260 nm at 75° C. indicated that the melting temperature of the duplex stem was 75° C. A melting temperature this high implies that the complex is very long lived, with an off rate of several days.

The results demonstrated that the 15 base 2'-OMe RNA stem binding GeneLead anchors and cleavers together into stable and functional antisense molecules, and that association occurred in the absence of target RNA, and in the presence of 1M urea. With a melting temperature of 75° C., the duplex stem is capable of binding GeneLead library member molecules together in solution, during cell transfection, and during the exertion of an antisense effect on specific target RNA molecules.

Example 7

Activity

Cleaver and anchor oligonucleotides were synthesized in decreasing lengths and tested for RNase H activation on SEAP. The following oligonucleotides were prepared:

TABLE 1

11/30 Cleaver and Anchor Molecules

| Oligo # | Cleaver or Anchor | SEQ ID NO: | Sequence* |
|---|---|---|---|
| 1000 | cleaver | 8 | 5'-GCUGGUUGAGUACUC9ggugggcgaauucgc |
| 1010 | anchor | 9 | 5'-GCUGGUUGAGUACUC9ggugggcgaauu |
| 1012 | anchor | 10 | 5'-GCUGGUUGAGUACUC9ggugggcg |
| 1013 | anchor | 11 | 5'-GCUGGUUGAGUACUC9gguggg |
| 1014 | anchor | 12 | 5'-GCUGGUUGAGUACUC9ggug |
| 1015 | cleaver | 13 | 5'-RGCAGCAGCAT + AGUACUCAACCAGC |
| 1016 | anchor | 14 | 5'-FGCUGGUUGAGUACUC + ggugggcgaa |

| Oligo # | SEQ ID NO: | Sequence |
|---|---|---|
| 1000‡ | 15 | 5'-CAGCAGCAGCAT9GAGUACUCAACCAGC |
| 1006‡ | 16 | 5'-GCAGCAGCAT9GAGUACUCAACCAGC |
| 1007‡ | 17 | 5'-AGCAGCAT9GAGUACUCAACCAGC |
| 1008‡ | 18 | 5'-CAGCAT9GAGUACUCAACCAGC |
| 1009‡ | 19 | 5'-GCAT9GAGUACUCAACCAGC |
| 1034‡ | 20 | 5'-CAGCAT-GAGUACUCAACCAGC |
| 1001‡ | 21 | 5'-GCUGGUUGAGUACUC9ggugggcgaauucgc |
| 1010‡ | 22 | 5'-GCUGGUUGAGUACUC9ggUgggcgaauu |
| 1011‡ | 23 | 5'-GCUGGUUGAGUACUC9ggugggcgaa |
| 1012‡ | 24 | 5'-GCUGGUUGAGUACUC9ggugggcg |
| 1013‡ | 25 | 5'-GCUGGUUGAGUACUC9gguggg |
| 1014‡ | 26 | 5'-GCUGGUUGAGUACUC9ggug |
| 1035‡ | 27 | 5'-GCUGGUUGAGUACUC-ggugggcg |
| 1045‡ | 28 | 5'-GCUGGUUGAGUACUC9ggugggcgaauucgc1 | where "ACGT" indicates phosphorothioate deoxyribonucleic acids, "ACGT" indicates 2'-O-methyl ribonucleic acid, "9" indicates Glen Research linker #9, "1" indicates Glen Research propyl linker on CPG, † indicates a cleaver oligo, and ‡ indicates an anchor oligo.

TABLE 3

RNase H activation-Cleaver Size

| Cleaver # | Cleaver binding length | Anchor # | Anchor binding length | RNA cleavage w/o anchor | RNA cleavage with anchor |
|---|---|---|---|---|---|
| 1000 | 12 | 1001 | 15 | +++++ | ++++++ |
| 1006 | 10 | 1001 | 15 | +++ | ++++ |
| 1007 | 8 | 1001 | 15 | ++ | +++ |
| 1008 | 6 | 1001 | 15 | – | + |
| 1009 | 4 | 1001 | 15 | – | – |

Figure 3:
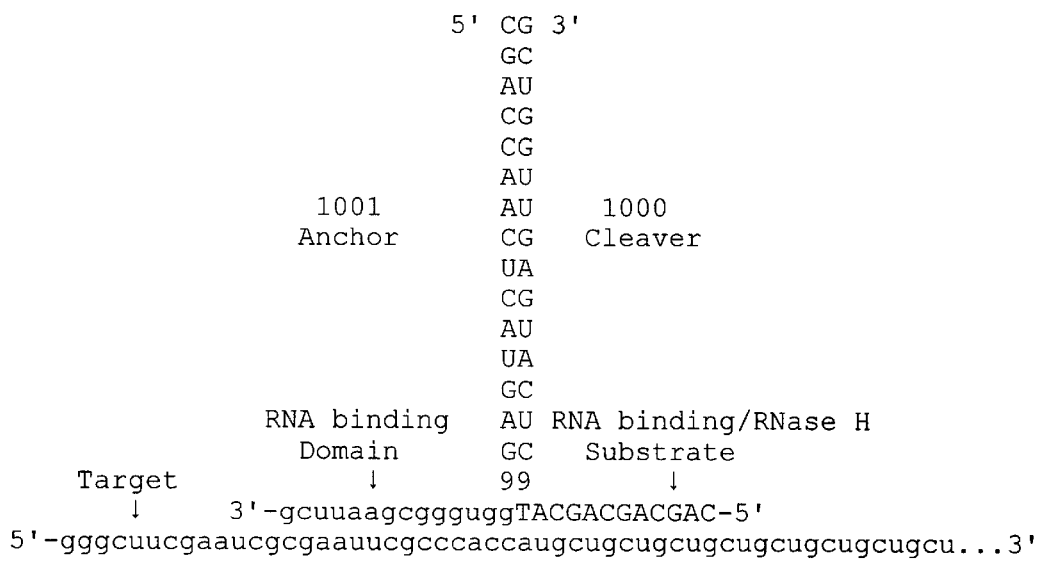
FIG. 3 illustrates a complex consisting of an anchor oligonucleotide (SEQ ID NO: 15), a cleaver oligonucleotide (SEQ ID NO: 21), and a target RNA (SEQ ID NO: 50).

All cleaver oligonucleotides resulted in more efficient cleavage when combined with the 1001 anchor. Cleaver 1008 was active only when combined with an anchor. Cleaver 1009 was inactive, in the presence and absence of the 1001 anchor molecule. The 1000/1001 (SEQ ID NO: 15/SEQ ID NO: 21) complex bound to a target polynucleotide (SEQ ID NO: 50) is illustrated in FIG. 3.

TABLE 4

RNase H activation-Anchor Size

| Cleaver # | Cleaver binding length | Anchor # | Anchor binding length | RNA cleavage w/o anchor | RNA cleavage with anchor |
|---|---|---|---|---|---|
| 1007 | 8 | — | NA | ++ | NA |
| 1007 | 8 | 1010 | 12 | NA | +++ |
| 1007 | 8 | 1011 | 10 | NA | +++ |
| 1007 | 8 | 1012 | 8 | NA | +++ |
| 1007 | 8 | 1013 | 6 | NA | ++++ |
| 1007 | 8 | 1014 | 4 | NA | +++ |

This data demonstrates that a cleaver of length 8 is capable of stimulating cleavage regardless of the length of any accompanying anchor, but that cleavage is maximized by an anchor of length 6.

Cleavers (six bases) and anchors (eight bases) were prepared with and without a 9-atom linker, and tested for RNase H activity.

| Oligo # | SEQ ID NO: | Sequence |
|---|---|---|
| 1019 | 29 | 5'-AGCABBBB9GAGUACUCAACCAGC |
| 1020 | 30 | 5'-AGCAGCBB9GAGUACUCAACCAGC |
| 1021 | 31 | 5'-BBBBGCAT9GAGUACUCAACCAGC |
| 1022 | 32 | 5'-KKPKKPKP9GAGUACUCAACCAGC |
| 1023 | 33 | 5'-KKPKGCAT9GAGUACUCAACCAGC | where "ACGTBK" indicate PS DNA, "ACGT" indicates 2-OMe RNA, and "9" indicates Glen Research linker #9. The results are set forth in Table 5 below:

TABLE 5

RNase H activity of oligonucleotides having linkers

| Cleaver # | Linker (y/n) | Anchor # | Linker (y/n) | RNA cleavage w/o anchor | RNA cleavage with anchor |
|---|---|---|---|---|---|
| 1008 | Y | none | NA | – | NA |
| 1008 | Y | 1012 | Y | NA | ++++ |
| 1008 | Y | 1035 | N | NA | ++ |
| 1034 | N | none | NA | – | NA |
| 1034 | N | 1012 | Y | NA | +++ |
| 1034 | N | 1035 | N | NA | + |

The result demonstrated increased activity when flexible linkers were used. The greatest activity was obtained when both cleaver and anchor contained a linker. In complexes having only one linker, the linker had the greatest effect when present in the anchor portion.

Cleavers and anchors were prepared incorporating modified bases. "Universal bases" ("B") do not significantly hydrogen bond to any natural base, but are tolerated in structure. "Degenerate bases" are those that hydrogen bond or fit in a duplex with either purines or pyrimidines ("K" and "P", respectively), but not both. By substituting a number of universal or degenerate bases for the natural bases in cleavers and/or anchors, one can prepare oligos having the ability to bind a greater number of target mRNA sequences.

TABLE 6

Activity with Cleaver length of 6 or 8

| Anchor # | Anchor binding length | Cleaver # | Cleaver binding length | RNA cleavage, w/o anchor | RNA cleavage, with anchor |
|---|---|---|---|---|---|
| none | NA | 1007 | 8 | ++ | NA |
| 1010 | 12 | 1007 | 8 | NA | +++ |

TABLE 6-continued

Activity with Cleaver length of 6 or 8

| Anchor # | Anchor binding length | Cleaver # | Cleaver binding length | RNA cleavage, w/o anchor | RNA cleavage, with anchor |
|---|---|---|---|---|---|
| 1013 | 6 | 1007 | 8 | NA | +++++ |
| 1014 | 4 | 1007 | 8 | NA | +++ |
| none | NA | 1008 | 6 | – | NA |
| 1010 | 12 | 1008 | 6 | NA | + |
| 1013 | 6 | 1008 | 6 | NA | ++ |
| 1014 | 4 | 1008 | 6 | NA | – |

The results from this experiment demonstrated that cleavers having a length of 8 bases were more effective in obtaining cleavage than 6 base cleavers, and that anchors having a length of 6 bases were more effective than 4 base or 12 base anchors.

TABLE 7

Activity with non-natural bases

| Cleaver # | N/B/P-K | Anchor # | RNA cleavage activity | Library size |
|---|---|---|---|---|
| 1007 | 8/0/0 | none | ++ | 65,536 |
| 1007 | 8/0/0 | 1013 | ++++ | 65,536 |
| 1009 | 4/4/0 | none | – | 256 |
| 1019 | 4/4/0 | 1013 | + | 256 |
| 1020 | 6/2/0 | none | ++ | 4096 |
| 1020 | 6/2/0 | 1013 | ++++ | 4096 |
| 1021 | 4/4/0 | none | – | 256 |
| 1021 | 4/4/0 | 1013 | – | 256 |
| 1022 | 0/0/8 | none | – | 256 |
| 1022 | 0/0/8 | 1013 | – | 256 |
| 1023 | 4/0/4 | none | – | 1024 |
| 1023 | 4/0/4 | 1013 | – | 1024 |
| 1052 | 6/0/6 | 1012 | ++ | 262,144 |

Propynyl pyrimidine bases and diaminopurine were used.

In Table 7 above, all cleavers have 8 bases, and the anchor has 6 bases. "N" indicates the number of natural bases, "B" indicates the number of universal bases, and "P-K" indicates the number of degenerate purine/pyrimidine bases. The "library size" is the number of molecules that would constitute every possible oligo of the size and composition set forth.

The results indicate that cleaver 1020, having 2 universal bases, bound as effectively as cleaver 1007 (having only natural bases), in the presence or absence of anchor oligos. Note that the size of the corresponding libraries is reduced by a factor of 16 by incorporating two universal bases.

Cleaver oligonucleotides including the universal base "B" having the sequences set forth in Table 8 were synthesized and tested for RNase H activity. The results are set forth in Table 9:

TABLE 8

Oligos

| Cleaver # | SEQ ID NO: | Sequence* |
|---|---|---|
| 1033 | 34 | 5'CAGCAT9ggugggcgl |
| 1025 | 35 | 5'GcAT9ggugggcgaauul |

TABLE 8-continued

Oligos

| Cleaver # | SEQ ID NO: | Sequence* |
|---|---|---|
| 1026 | 36 | 5'AGCABBBB9ggugggcgaauul |
| 1027 | 37 | 5'GCBB9ggugggcgaauul |

*C, G, A, T = phosphorothioate DNA: c, g, u, a = 2'-O-Me phosphorothioate RNA; "9" = Glen Research Liner #9, "1" = Glen Research propyl linker

TABLE 9

Cleaver oligonucleotides including B

| Cleaver # | 2'O-Me/RNase H/Universal bases | Anchor # | RNA cleavage |
|---|---|---|---|
| 1033 | 8/6/0 | None | ++ |
| 1025 | 12/4/0 | None | – |
| 1026 | 12/8/4 | None | +++ |
| 1027 | 12/2/2 | None | – |
| 1019 | 6/8/4 | 1013 | + |
| 1020 | 6/8/2 | 1013 | ++++ |

The presence of a flexible linker between the RNase H recognition region and the 2'-OMe RNA binding region of 1033 does not eliminate the antisense activity. This linker appears to be tolerated serves as a model for other ways to join a target-cleaving region and target region to form a single, active antisense molecule. Other ways of joining cleavers and anchors, two short cleavers, and other library-based oligonucleotide structures will (for example chelation and post-synthetic covalent interaction) may be substituted.

The RNase H activity of 1033 (in comparison to 1025) clearly demonstrates a length dependence on RNase H recognition. Even thought the overall length of the molecule is longer for 1025, it is less active than 1033. The key difference appears to be in the length of the short, all-phosphorothioate (PS) region. A 4-base PS region at the end of the molecule appears to be too short for efficient cleavage. Thus, 1027 is most likely inactive due to the fact that the RNase H substrate PS region is only 4 bases long, and not due to the 2 universal bases.

A comparison of the RNase H activity of 1033 (a single, linear antisense molecule) with the 1020/1013 pair demonstrates the dependence on the length of the RNase H substrate region. The 1020/1013 pair, containing two universal bases and a duplex stem holding the structure together, is significantly more active than 1033, which contains no universal bases, no stem structure, and has exactly the same footprint length on the SEAP target mRNA.

The two universal bases contained in 1020 appear to lengthen the all-PS RNase H recognition region just enough, to 8 total bases, that the target RNA is cleaved much more efficiently than RNA hybridized to the 6 base substrate region of 1033. The critical step of including universal bases to avoid increasing the numerical complexity of an antisense library is graphically demonstrated by these results. The 6 base PS region of 1033 contributes a factor of 4,096 to any library based on this linear, linker-containing oligonucleotide. Adding two natural bases to the PS region to improve its RNase H substrate activity would increase the factor by $4^2$, to a total of 65,536. The fact that the 1020/1013 pair, containing two universal bases and a bulky 2'-OMe duplex stem coupler, is more active than a linear molecule is surprising.

Example 8

Intracellular Activity

Protein Kinase C Alpha (PKCα) was chosen as the gene target to demonstrate activity inside human cells. PKCα is a normal human gene that is overexpressed in a majority of human cancer types, and is one of the most highly publicized of all antisense target genes.

The oligonucleotides prepared for this example are listed in Table 10.

TABLE 10

Oligonucliotides

| Oligo # | SEQ ID NO: | Cleaver/ Anchor | Sequence* |
|---|---|---|---|
| 1040 | 38 | cleaver | 5'GTTCTCGCTGGT9GAGUACUCAACCAGC1 |
| 1041 | 39 | anchor | 5'GCUGGUUGAGUACUC9gaguuuca |
| 1042 | 40 | control cleaver | 5'TGTGTTACCATC9GAGUACUCAACCAGC1 |
| 1043 | 41 | control anchor | 5'GCUGGUUGAGUACUC9gguugcgu |
| 1058 | 42 | ISIS3521 antisense | 5'GTTCTCGCTGGTGAGTTTCA |
| 1059 | 43 | ISIS4189 control | 5'GGTTTACCATCGGTTCTGG |
| 1061 | 44 | BCL2 4 mismatch control | 5'TCTACCCGCGTCCGGCAT |

*C, G, A, T = phosphorothioate DNA: c, g, u, a = 2'-O-Me phosphorothioate RNA; C, G, A, T = 2'-OMe RNA; "9" = Glen Research Linker #9, "1" = Glen Research propyl linker Oligo 1040 (a 12-mer, RNase H-substrate cleaver) hybridized to 1041 (an 8-mer, non-RNase H-substrate anchor) to create an active antisense construction against PKCα. Oligos 1042 and 1043 were a control clever and anchor, respectively, that hybridized together to form a construct that does not match a known gene, but has the same base composition as 1059 (ISIS4189), a control all-phosphorothioate oligonucleotide 20-mer. Oligo 1058 (ISIS3551) was a conventional 20 mer all-phosphorothioate antisense oligonucleotide that has been well established to act via an antisense mechanism to down regulate the expression of PKCα. Oligo 1061 was a conventional all-phosphorothioate 18 mer, 4 base mismatch control to the BCL2 gene.

A human bladder carcinoma line (T-24, ATCC HTB-4), a cell line known to over-express PCKα, was used in the experiments. T-24 was maintained in culture using standard methods: 37° C., 5% $CO_2$, in 75 $cm^2$ flasks (Falcon, 3084) in McCoy's 5A medium (Mediatech, #10-050-CV) with 10% serum (Gemini Bio-Products, #100-107) and penicillin-streptomycin (50 IU/ml, 50 µg/ml, Mediatech #30-001-LI). For antisense experiments, T-24 cells were plated into 12-well plates (Falcon, #3043) at 75,000 cells/ well and allowed to adhere and recover overnight before transfection.

Oligonucleotides were transfected into T-24 cells with a cationic lipid-containing cytofection agent (LipofectACE™, GibcoBRL, #18301-010), which provides efficient nuclear delivery of fluorescently labeled oligonucleotides of the invention in T-24.

Oligonucleotides of the invention and conventional all-phosphorothioate oligonucleotides were diluted into 1.5 mL of reduced serum medium Opti-MEM® I (Gibco-BRL, #11058-021) to a concentration of 400 nM each. The oligonucleotide-containing solutions were then mixed with an equal volume of Opti-MEM I containing LipofectACE sufficient to give a final lipid to oligonucleotide ratio of 5 to 1 by weight. The final concentration of oligonucleotide was 200 nM. The oligonucleotide/lipid complexes were incubated at room temperature for 20 minutes before adding to tissue culture cells.

Cells were washed once in phosphate buffered saline (PBS, Mediatech, #21-030-LV) to rinse away serum-containing medium, and then transfection mix (1 ml) was placed in each well of a 12-well plate. All transfections were performed in triplicate. The cells were allowed to take up oligonucleotide/lipid complexes for 22 hours prior to harvesting the total cellular RNA. Mock transfections consisted of cells treated with Opti-MEM I only.

Total Cytoplasmic RNA Isolation: After 22 hours of antisense treatment, total RNA was harvested from the cells. The cells were released from the plates by trypsinizing (Trypsin/EDTA, Mediatech #25-052-LI) according to standard methods. The triplicate groups of cells were pooled and total cytoplasmic RNA was isolated using an RNeasy Kit (QIAGEN, #74104) according to manufacturer's protocols. The RNA was DNase I treated and UV quantitated according to standard methods.

Polymerase Chain Reactions to Detect PKCα RNA: Reverse Transcriptase/Polymerase Chain Reactions (RT-PCR) were performed with the methods and materials from a SuperScript One-Step RT-PCR Kit from GibcoBRL (Cat. No. 10928-026). The RT-PCR reactions to detect PKCα were performed in two independent runs, with PKCα-specific primers from Oxford Biomedical Research (#EZ-60A and EZ-60B) and 100 ng of input total RNA.

Control Multiplex RT-PCRs (MP RT-PCRs) were performed to confirm equal quantities of input RNA into each PKCα RT-PCR. The primers, reagents, and protocol were from Maxim Biotech (#APO-M052-G). The control MP RT-PCRs amplified BAX and LICE genes equally in all samples, confirming that equal amounts of intact RNA were added to the PKCα RT-PCRs.

All RT-PCR reactions were performed according to the following program on a PTC-100 thermocycler (MJResearch): Step 1, 50° C. for 35 minutes; Step 2, 94° C. for 2 minutes; Step 3, 55° C. for 30 seconds; Step 4, 72° C. for 1 minute; Step 5, 94° C. for 30 seconds; Step 6, Go to Step 3, 33 more times; Step 7, 72° C. for 10 minutes; Step 8, End. All RT-PCR products were separated on a 4% Super Resolution Agarose TBE gel (Apex, #20-105) and stained with CyberGold (Molecular Probes, #S-11494), according to the manufacturer's instructions. Gels were photographed on Polaroid Type 667 film. The results are set forth in Table 11.

TABLE 11

| | Intracellular RNase H activity | | | | |
|---|---|---|---|---|---|
| Treatment | 1st oligo | 2nd oligo | PKCα | BAX | LICE |
| Mock treatment | — | — | ++++ | ++++ | +++ |
| Cleaver alone | 1040 | — | ++++ | ++++ | +++ |
| Anchor alone | — | 1041 | ++++ | ++++ | +++ |
| Anchor + Cleaver | 1040 | 1041 | + | ++++ | +++ |
| Control | 1042 | 1043 | ++++ | ++++ | +++ |
| Conventional antisense | 1058 | — | + | ++++ | +++ |
| Conventional control | 1059 | — | ++++ | ++++ | +++ |
| Conventional control | 1061 | — | ++++ | ++++ | +++ |

The oligonucleotide constructs of the invention proved to be as active as conventional 20 mer phosphorothioate oligonucleotides, as demonstrated by the anchor+cleaver vs conventional antisense above. Note that neither cleaver (1040) nor anchor (1041) demonstrated any activity when administered alone, but demonstrated full activity when assembled. The control GeneLead construct (1042+1043) showed no non-specific activity against PKCα, BAX or LICE, nor did any of the other control oligonucleotides.

The results demonstrate that GeneLead constructs are as active as conventional antisense molecules. Further, the GeneLead constructs can be assembled from a standing, pre-synthesized library of components, which is not feasible with conventional antisense molecules.

Example 9

Activity Against the Human Bcl2 Gene in Tissue Culture Cells

B-cell Lymphoma-Associated Gene 2 (BCL2) was chosen to demonstrate GeneLead™ activity inside human cells. BCL2 is another "normal" human gene that is over expressed in a majority of human cancer types. The BCL2 protein is one of a large family of proteins that regulate cell death. BCL2 over expression is known to cause cells to be chemotherapy and radiotherapy resistant.

and penicillin-streptomycin (50 IU/mL, 50 mcg/mL, Mediatech, Cat. No. 30-001-LI).

For antisense experiments T-24 were plated into 12-well plates (Falcon, Cat. No. 3043) at 75,000 cells/well and allowed to adhere and recover overnight before oligonucleotide transfections began.

Transfection of Oligonucleotides into T-24 cells: Oligonucleotides were transfected into T-24 cells with a cationic lipid-containing cytofectin agent LipofectACE™ (GibcoBRL, Cat. No. 18301-010). LipofectACE has been shown to give efficient nuclear delivery of fluorescently labeled GeneLead constructions in T-24.

GeneLead and conventional all-phosphorothioate oligonucleotides were diluted into 1.5 mL of reduced serum medium Opti-MEM© I (GibcoBRL, Cat. No. 11058-021) to a concentration of 400 nM each. The oligonucleotide-containing solutions were then mixed with an equal volume of Opti-MEM I containing LipofectACE sufficient to give a final lipid to oligonucleotide ratio of 5 to 1 by weight.

The final concentration of oligonucleotide was 200 nM. The oligonucleotide/lipid complexes were incubated at room temperature for 20 minutes before adding to tissue culture cells.

Cells were washed once in phosphate buffered saline (PBS, Mediatech Cat. No. 21-030-LV) to rinse away serum-

```
1060 BCL2 18-base antisense      5'TCTCCCAGCGTGCGCCAT (SEQ ID
                                 NO:45)
1061 BCL2 4 mismatch control     5'TCTACCCGCGTCCGGCAT (SEQ ID
                                 NO:46)
1062 BCL2 GeneLead Cleaver       5'TCTCCCAGCGTG9GAGUACUCAACCAGC1
                                 (SEQ ID NO:47)
1063 BCL2 GeneLead Cleaver       5'TCTCCCAGCGBB9GAGUACUCAACCAGC1
                                 (SEQ ID NO:48)
1066 BCL2 GeneLead Anchor        5'GCUGGUUGAGUACUC9cgccat1 (SEQ
                                 ID NO:49)
``` where NNNN=phosphorothioate deoxyribonucleic acid (PS DNA), NNNN=2'-O-methyl ribonucleic acid (2'-OMe RNA), nnnn=2'-O-Methyl phosphorothioate ribonucleic acid (2'-OMe PS RNA), and NNNN=C-5 Propynyl-modified phosphorothioate deoxyribonucleic acid (Propynyl), 9=Glen Research linker #9, 1=Glen Research propyl linker on CPG (Cat. No. **), F=Molecular Probes Fluorescein (Cat. No. F-1907), and R=Molecular Probes Rhodamine (Cat. No. X-491).

1062 (a 12-mer, RNase H-substrate cleaver) and 1063 (a 12-mer, RNase H-substrate cleaver with a 6-base C-5 propynyl-modified "tack" at the 5' end of the RNase H-substrate region) both hybridized to 1066 (a 6-mer, non-RNase H-substrate anchor) to create active GeneLead antisense constructions against BCL2.

1060 (based on a published oligonucleotide known clinically as G3139) is a conventional 18-mer all-phosphorothioate antisense oligonucleotide. 1060 hybridizes to the BCL2 pre-mRNA across the first 6 codons of the open reading frame.

1061 is a conventional all-phosphorothioate 18-mer, 4 base mismatch control to the BCL2 gene.

Tissue Culture: The cell line that was used for this demonstration was T-24 (American Type Culture Collection #HTB-4), a human bladder carcinoma line known to over express BCL2.

T-24 was maintained in culture using standard methods at 37° C., 5% $CO_2$, in 75-$cm^2$ flasks (Falcon, Cat. No. 3084) in McCoy's 5A medium (Mediatech, Cat. No. 10-050-CV) with 10% serum (Gemini Bio-Products, Cat. No. 100-107)

containing medium and then one mL of transfection mix was placed into each well of a 12-well plate. All transfections were performed in triplicate.

The cells were allowed to take up oligonucleotide/lipid complexes for 24 hours prior to harvesting of total cellular RNA. Mock transfections consisted of cells treated with Opti-MEM I only.

Total Cytoplasmic RNA Isolation: After 22 hours of antisense treatment, total RNA was harvested from the cells. The cells were released from the plates by trypsinizing (Trypsin/EDTA, Mediatech Cat. No. 25-052-LI) according to standard methods. The triplicate groups of cells were pooled and total cytoplasmic RNA was isolated according to the RNeasy Protocol and spin columns from an RNeasy Kit (QIAGEN, Cat. No. 74104).

The RNA was DNase I treated and UV quantitated according to standard methods.

Polymerase Chain Reactions to Detect BCL2 RNA: Reverse Transcriptase/Polymerase Chain Reactions (RT-PCR) were performed with the methods and materials from a SuperScript One-Step RT-PCR Kit from GibcoBRL (Cat. No. 10928-026). The RT-PCR reactions to detect BCL2 were performed with BCL2-specific primers from the literature: upstream 5'ggtgccacctgtggtccacctg (SEQ ID NO: 51) and downstream 5'cttcacttgtggcccagatagg (SEQ ID NO: 52) (both primers were normal DNA and 1 μg of input total RNA. Control RT-PCR reactions against β-actin were also performed with primers from the literature: upstream 5'gagctgcgtgtggctcccgagg (SEQ ID NO: 53) and downstream 5'cgcaggatggcatgggggggcatacccc (SEQ ID NO: 54) (both primers were normal DNA) and 0.1 g of input total RNA.

All BCL2 and β-actin RT-PCR reactions were performed according to the following program on a PTC-100 thermocycler (MJResearch): Step 1, 50° C. for 35 minutes; Step 2, 94° C. for 2 minutes; Step 3, 60° C. for 30 seconds; Step 4, 72° C. for 1 minute; Step 5, 94° C. for 30 seconds; Step 6, Go to Step 3, 35 more times; Step 7, 72° C. for 10 minutes; Step 8, End.

All RT-PCR products were separated on a 4% Super Resolution Agarose TBE gel (Apex, Cat. No. 20-105) and stained with SyberGold (Molecular Probes, Cat. No. S-11494), according to the manufacture's instructions. Gels were photographed on Polaroid Type 667 film.

TABLE 12

Reduced Target Gene Expression (BCL2) Confirms that GeneLead Constructions With Universal Bases Are Active and Specific in Cells

| Lane | Treatment | Cleaver Oligo | Anchor Oligo | All-PS Oligo | BCL2 mRNA level | β-actin mRNA level |
|---|---|---|---|---|---|---|
| 1 | Mock | — | — | — | ++++ | ++++ |
| 2 | Conventional antisense | — | — | 1060 | + | ++++ |
| 3 | Conventional control | — | — | 1061 | ++++ | ++++ |
| 4 | Cleaver alone | 1062 | — | — | ++++ | ++++ |
| 5 | GeneLead assembled | 1062 | 1066 | — | + | ++++ |
| 6 | Cleaver alone | 1063 | — | — | +++ | ++++ |
| 7 | GeneLead assembled | 1063 | 1066 | — | + | ++++ |
| 8 | Anchor alone | — | 1066 | — | ++++ | ++++ |

Results

The GeneLead anti-BCL2 constructions dropped BCL2 RNA levels significantly compared to control treatments. Compare lanes 5 (oligos 1062+1066) and 7 (1063+1066) to lanes 1 (mock treatment) and 3 (conventional antisense control).

None of the oligonucleotides and GeneLead constructions showed any activity against the control gene β-actin.

This is significant because it clearly demonstrates GeneLead activity with: (a) only a 6 base anchor (1066, lanes 5 and 7), (b) two nitroindole universal bases, "B", replacing natural bases in the cleaver sequence (1063 alone, and 1063+1066, lanes 6 and 7), and (c) that GeneLead activity is general and could be easily observed against another human target genes.

The experimental result that an anchor as short a 6 bases long combined with a cleaver containing nitroindole as a universal base (1063+1066) could form a GeneLead construct with effective antisense activity inside cells clearly confirmed the validity of our cell-free work with SEAP-targeted GeneLead oligonucleotides.

The principles of separating oligonucleotides into two or more functional units and incorporating universal bases in order to numerically simplify combinatorial libraries of antisense oligonucleotides has been reduced to practice in living human cells.

These concepts can easily be applied to improve current uses of oligonucleotides in diagnostics, ribozyme applications, and immuno-stimulation (CpG oligonucleotides).

REFERENCES

Ramon Eritja et al., "Synthesis and properties of defined DNA oligomers containing base mispairs involving 2-aminopurine" Nuc Acids Res (1986) 14(14):5869–85

Stefan Pitsch et al., "Why Pentose-and Not Hexose-Nucleic Acids?" Helv Chimica Acta (1993) L6:2161–83

P. Kong Thoo Lin et al., "Synthesis and duplex stability of oligonucleotides containing cytosinethymine analogues" Nuc Acids Res (1989) 17(24):10373–83

Daniel M. Brown et al., "Synthesis and duplex stability of oligonucleotides containing adenine-guanine analogues" Carbohydrate Res (1991) 216:129–39

D. Loakes et al., "5-Nitroindole as an universal base analogue" Nuc Acids Res (1994) 22(20):4039–43

Novabiochem Catalog and Peptide Synthesis Handbook, 1997–1998, pp. S1–S88

E. Hochuli et al., "New Metal Chelate Adsorbent Selective for Proteins and Peptides Containing Neighboring Histidine Residues" J.Chromatog (1987) 411:177–84

Eric E. Swayze et al. "The Synthesis of N,N'-O-Trisubstituted Hydroxylamines via a Mild Reductive Alkylation Procedure: An Improved Synthesis of the MMI Backbone" Synlett (1997) 859–861.

Francois Morvan et al. "Oligonucleotide Mimics for Antisense Therapeutics:Solution Phase and Automated Solid-Support Synthesis of MMI Linked Oligomers" J Am Chem Soc (1996) 118:255–56

Michel Perbost et al. "Synthesis of 5'-O-Amino-2'deoxypyrimidine and Purine Nucleosides: Building Blocks for Antisense Oligonucleotides" J. Org. Chem. (1995) 60:5150–56

Antivirals Inc., "General Properties of Morpholino Oligomers", Technical Bul#1, 1998

Kim L. Dueholm et al. "Synthesis of Peptide Nucleic Acid Monomers Containing the Four Natural Nucleobases: Thymine, Cytosine, Adenine, and Guanine and their Oligomerization" J. Org. Chem. (1994) 59:5767–73

Jeffrey S. Nelson et al. "N3'-P5' Oligodeoxyribonucleotide Phosphoramidates: A New Method of Synthesis Based on a Phosphoramidite Amine-Exchange Reaction" J. Org. Chem. (1997) 62:7278–87

Jer-Kang Chen et al. "Synthesis of Oligodeoxyribonucleotide N3'-P5' phosphoramidates" Nuc Acids Res (1995) 23(14):2661–68

Sarah N. McCurdy et al. "An Improved Method for the Synthesis of N3'-P5' Phosphoramidate Oligonucleotides" Tetrahedron Lett (1997) 38(2):207–10

What is claimed:

1. A method of cleaving a target RNA in a cell in culture, comprising:

determining a cleavage site on a target RNA;

selecting a first oligonucleotide analog that binds to said cleavage site, wherein said first oligonucleotide analog further comprises a first coupling domain;

selecting a second oligonucleotide analog that binds to said cleavage site, wherein said second oligonucleotide analog further comprises an RNAse recognition region and a second coupling domain;

combining said first oligonucleotide analog and said second oligonucleotide analog whereby said first coupling domain and said second coupling domain spontaneously bind together in the absence of said target RNA to form a dimer;

introducing said dimer into said cell in culture; and contacting said dimer with said target RNA under conditions that form a complex and allow said dimer and target RNA complex to act as an endonuclease substrate wherein the second oligonucleotide analog only binds to the target RNA and activates an RNAse when the first and second coupling domains are bound together.

2. A method for cleaving a target RNA molecule, comprising:

providing a target RNA molecule;

contacting the target RNA molecule with a first oligonucleotide analog comprising a first binding domain which binds a first region of said target RNA molecule, and a first coupling moiety capable of binding to a second coupling moiety; contacting the target RNA molecule with a second oligonucleotide analog comprising a second binding domain capable of binding a second region of said target RNA molecule, an RNase recognition region and a second coupling moiety which binds to said first coupling moiety, wherein said first and second coupling moieties self-assemble in the absence of said target RNA molecule, and wherein said first and second binding domains bind simultaneously to said target RNA molecule, and wherein said second binding domain does not bind the target RNA molecule and activate RNase unless the first and second coupling moieties are bound; and incubating said target RNA molecule, first oligonucleotide analog and second oligonucleotide analog in the presence of an RNase, wherein said incubating results in cleavage of the RNA target.

3. The method of claim 2, wherein said first and second binding domains each independently comprise from about 3 to about 24 bases.

4. The method of claim 2, wherein said first region and second region are non-overlapping.

5. The method of claim 2, wherein said second binding domain and said second coupling moiety are joined together by a flexible linker.

6. The method of claim 5, wherein said first binding domain and said first coupling moiety are joined together by a flexible linker.

7. The method of claim 2, wherein said incubating is intracellular.

\* \* \* \* \*